US009693826B2

(12) United States Patent
Neuberger

(10) Patent No.: US 9,693,826 B2
(45) Date of Patent: Jul. 4, 2017

(54) ENDOLUMINAL LASER ABLATION DEVICE AND METHOD FOR TREATING VEINS

(75) Inventor: Wolfgang Neuberger, Dubai (AE)

(73) Assignee: biolitec Unternehmensbeteiligungs II AG, Vienna (AT)

( * ) Notice: Subject to any disclaimer, the term of this patent is extended or adjusted under 35 U.S.C. 154(b) by 1027 days.

(21) Appl. No.: 12/395,455

(22) Filed: Feb. 27, 2009

(65) Prior Publication Data
US 2009/0240242 A1    Sep. 24, 2009

Related U.S. Application Data

(60) Provisional application No. 61/104,956, filed on Oct. 13, 2008, provisional application No. 61/079,024, filed on Jul. 8, 2008, provisional application No. 61/067,537, filed on Feb. 28, 2008.

(51) Int. Cl.
*A61B 18/18*   (2006.01)
*A61B 18/24*   (2006.01)
*A61B 17/22*   (2006.01)
*A61B 18/22*   (2006.01)

(52) U.S. Cl.
CPC ........ *A61B 18/24* (2013.01); *A61B 17/22012* (2013.01); *A61B 2018/2272* (2013.01)

(58) Field of Classification Search
CPC .................. A61B 18/245; A61B 18/24; A61B 2017/22038; A61B 2017/22041; A61B 2017/22047
USPC ........................................................... 606/7
See application file for complete search history.

(56) References Cited

U.S. PATENT DOCUMENTS

| | | | | |
|---|---|---|---|---|
| 4,785,815 A | * | 11/1988 | Cohen .............................. | 606/15 |
| 4,850,351 A | * | 7/1989 | Herman et al. ................... | 606/7 |
| 5,029,588 A | * | 7/1991 | Yock et al. .................... | 600/471 |
| 5,037,172 A | * | 8/1991 | Hekman et al. ................ | 385/31 |
| 5,242,438 A | * | 9/1993 | Saadatmanesh et al. ....... | 606/15 |

(Continued)

OTHER PUBLICATIONS

P. Timperman, M. Sichlau, R. Ryu, Greater Energy Delivery Improves Treatment Success of Endovenous Laser Treatment of Incompetent Saphenous Veins, Journal of Vascular and Interventional Radiology, vol. 15, Issue 10, pp. 1061-1063 (2004).

*Primary Examiner* — John R Downey
(74) *Attorney, Agent, or Firm* — BJ Associates; Bolesh J Skutnik

(57) ABSTRACT

An improved method and device is provided for safe and efficient low power density endoluminal treatment of venous insufficiency. One such device emits pulsed or continuous energy radially through an optical fiber end with a conical shaped tip for 360° radial emission. In some embodiments, a conical reflective surface is distally spaced opposite to and faces the emitting tip for enhancing radial emission efficiency by reflecting out any designed or remnant forwardly transmitted energy in radial directions. Other devices include flat emitting faces sealed within protective, radiation transparent covers. Laser radiation is transmitted at a wavelength and power such that is it substantially entirely absorbed within the blood vessel wall to sufficiently damage the intravascular endothelium and, in turn, achieve blood vessel closure. Because the energy is substantially entirely absorbed within the blood vessel wall, the need for a local anesthetic along the treatment area of the blood vessel may be substantially avoided.

38 Claims, 10 Drawing Sheets

(56) References Cited

U.S. PATENT DOCUMENTS

| | | | |
|---|---|---|---|
| 5,261,904 A * | 11/1993 | Baker et al. | 606/17 |
| 5,292,320 A * | 3/1994 | Brown et al. | 606/15 |
| 5,303,324 A * | 4/1994 | Lundahl | 385/147 |
| 5,370,649 A * | 12/1994 | Gardetto et al. | 606/17 |
| 5,562,657 A * | 10/1996 | Griffin | 606/17 |
| 6,056,743 A * | 5/2000 | Ellis et al. | 606/15 |
| 6,102,905 A * | 8/2000 | Baxter et al. | 606/15 |
| 6,132,423 A * | 10/2000 | Aita et al. | 606/7 |
| 6,200,332 B1 | 3/2001 | Del Giglio | |
| 6,352,531 B1 * | 3/2002 | O'Connor et al. | 606/15 |
| 6,398,777 B1 | 6/2002 | Navarro et al. | |
| 6,402,745 B1 | 6/2002 | Wilk | |
| 6,620,153 B2 * | 9/2003 | Mueller et al. | 606/15 |
| 6,986,766 B2 | 1/2006 | Caldera et al. | |
| 7,108,692 B2 * | 9/2006 | Frenz et al. | 606/15 |
| 7,238,179 B2 * | 7/2007 | Brucker et al. | 606/15 |
| 2003/0199860 A1 * | 10/2003 | Loeb et al. | 606/17 |
| 2004/0199151 A1 | 10/2004 | Neuberger | |
| 2005/0131400 A1 * | 6/2005 | Hennings et al. | 606/15 |
| 2006/0069417 A1 | 3/2006 | Farley et al. | |
| 2006/0133750 A1 * | 6/2006 | Lee | G02B 6/001 385/115 |
| 2007/0071389 A1 * | 3/2007 | Yoon | G02B 6/02066 385/37 |
| 2008/0300576 A1 * | 12/2008 | Vitullo et al. | 604/523 |

\* cited by examiner

ENDOLUMINAL LASER ABLATION DEVICE AND METHOD FOR TREATING VEINS

CROSS REFERENCE TO PRIORITY APPLICATION

This patent application claims priority to U.S. provisional patent application No. 61/104,956, filed Oct. 13, 2008, entitled "Endoluminal Laser Ablation Device And Method For Treating Veins", U.S. provisional patent application No. 61/079,024, filed 8 Jul. 2008, entitled "Radial Emitting Device And Method For Treating Veins", and U.S. provisional patent application No. 61/067,537, filed 28 Feb. 2008, entitled "Rapid Insertion Device And Method For Improved Vascular Laser Treatment", each of which is hereby expressly incorporated by reference in its entirety as part of the present disclosure.

BACKGROUND OF THE INVENTION

Field of the Invention

The present invention relates to laser endovascular treatments, and more particularly, to the treatment of vascular pathologies, such as venous insufficiency, with laser energy using an optical fiber.

Information Disclosure Statement

The human venous system of the lower limbs consists essentially of the superficial venous system and the deep venous system, both connected by perforating veins. The superficial system comprises the great and the small saphenous veins, while the deep venous system includes the anterior and posterior tibial veins, which converge to form the popliteal vein near the knee. The popliteal vein, in turn, becomes the femoral vein when joined by the small saphenous vein.

The venous system comprises valves that function to achieve unidirectional blood flow back to the heart. Venous valves are bicuspid valves wherein each cusp forms a blood reservoir. The bicuspid venous valves force their free surfaces together under retrograde blood pressure. When properly operating, retrograde blood flow is prevented, allowing only antegrade flow to the heart. A bicuspid valve becomes incompetent when its cusps are unable to seal properly under a retrograde pressure gradient such that retrograde blood flow occurs. When retrograde blood flow occurs, pressure increases in the lower venous sections which can, in turn, dilate veins and lead to additional valvular failure.

Valvular failure, usually referred to as venous insufficiency, is a chronic disease that can lead to skin discoloration, varicose veins, pain, swelling and ulcerations. Varicose veins are blood vessels that have become enlarged and twisted and have progressively lost elasticity in their walls. Due to the widening of the blood vessels, the valves cannot be completely closed and the veins lose their ability to carry blood back to the heart. This leads to an accumulation of blood inside the vessels which can, in turn, further enlarge and twist the veins. Varicose veins usually have a blue or purple color and may protrude in a twisted form above the surface of the skin giving rise to a characteristically unattractive appearance. Varicose veins are commonly formed in the superficial veins of the legs, which are subject to high pressure when standing. Other types of varicose veins include venous lakes, reticular veins and telangiectasias.

There are a number of treatments available for eradicating these types of vascular pathologies. Some such treatments only operate to relieve certain symptoms but do not eliminate the varicose veins or prevent them from reforming. These treatments include elevating the legs by lying down or using a footstool when sitting, elastic stockings and exercise.

Varicose veins are frequently treated by eliminating the insufficient veins. These treatments force the blood that otherwise would flow through the eliminated vein to flow through the remaining healthy veins. Various methods can be used to eliminate problematic insufficient veins, including surgery, sclerotherapy, electro-cautery, and laser treatments.

Sclerotherapy uses a fine needle to inject a solution directly into the vein. This solution irritates the lining of the vein, causing the lining to swell and the blood to clot. The vein turns into scar tissue that may ultimately fade from view. Some physicians treat both varicose and spider veins with sclerotherapy. Today, commonly used sclerosants include hypertonic saline or Sotradecol™ (sodium tetradecyl sulfate). The sclerosant acts upon the inner lining of the vein walls to cause them to occlude and block blood flow. Sclerotherapy can give rise to a variety of complications. People with allergies may suffer allergic reactions which at times can be severe. If the needle is not properly inserted, the sclerosant can burn the skin or permanently mark or stain the skin. In addition, sclerotherapy can occasionally lead to blood clots or traveling blood clots. According to some studies, larger varicose veins may be more likely to reopen when treated with sclerotherapy, and therefore sclerotherapy treatments are generally limited to veins below a particular size.

Vein stripping is a surgical procedure used to treat varicose veins under general or local anesthesia. The problematic veins are stripped from the body by passing a flexible device through the vein and removing it through an incision near the groin. Smaller tributaries of these veins also are stripped with such a device or are removed through a series of small incisions (e.g., by ambulatory phlebectomy). Those veins that connect to the deeper veins are then tied off.

One drawback of vein stripping procedures is that they can cause scarring where the incisions are made and occasionally may cause blood clots. Another drawback is that vein stripping can be painful, time consuming to perform, and can require lengthy recovery periods. Yet another drawback of vein stripping procedures is that they can damage collateral branches of the stripped vein which may bleed and, in turn, give rise to hematomas, or lead to other complications, such as blood loss, pain, infection, nerve injury and swelling. Yet another drawback of vein stripping is that because of the damage done to the treated area, patients may have pain and discomfort for many hours, if not many days following surgery. Another drawback of vein stripping procedures is that they can include other negative side effects associated with performing such surgical procedures under anesthesia, including nausea, vomiting, and the risk of wound infection.

Another well known method of treating insufficient veins is through the use of radio frequency ("RF"). An exemplary RF method is described in U.S. Patent Application No. 2006/0069471 to Farley et al. Electrodes are introduced through a catheter inside the vein, the electrodes are placed in contact with the vein wall, and RF energy is applied through the electrodes to selectively heat the vein wall. RF energy is applied in a directional manner through the electrodes and into the portions of the vein wall that are in contact with the electrodes to cause localized heating and fibrosis of the venous tissue. One drawback of RF methods is that they require maintained contact between the RF electrodes and the vein wall and thus deliver energy to the vein wall essentially only through such points of contact. Yet another drawback of RF methods is that they can be more time consuming and thus more stressful to the patient than otherwise desired. Yet another drawback of RF methods is that the RF catheters and electrodes can be relatively complex and more expensive to manufacture than otherwise desired.

Another minimally invasive prior art treatment for varicose veins is endoluminal laser ablation ("ELA"). In a typical prior art ELA procedure, an optical fiber is introduced through an introducer sheath into the vein to be treated. The fiber optic line has a flat emitting face at its distal end. An exemplary prior art ELA procedure includes the following steps: First, a guide wire is inserted into the vein to be treated, preferably with the help of an entry needle. Second, an introducer sheath is introduced over the guide wire and advanced to a treatment site. Then, the guide wire is removed leaving the introducer sheath in place. The optical fiber (coupled to a laser source) is then inserted through the introducer sheath and positioned so that the flat emitting face at the distal tip of the fiber and the sheath are at the same point. Tumescent anesthesia is then applied to the tissue surrounding the vein to be treated. Prior to lasing, the sheath is pulled back from the flat emitting face a distance sufficient to prevent the emitted laser energy from damaging the sheath. Then, the laser is fired to emit laser energy through the flat emitting face and into the blood and/or vein wall directly in front of the emitting face. While the laser energy is emitted, the laser fiber and introducer sheath are withdrawn together to treat and close a desired length of the vein. The laser energy is absorbed by the blood and/or vein wall tissue and, in turn, thermally damages and causes fibrosis of the vein.

U.S. Pat. No. 6,200,332 to Del Giglio discloses an exemplary prior art device and method for under skin laser treatment with minimal insertions into the area of treatment. Common vascular abnormalities such as capillary disorders, spider nevus, hemangioma, and varicose veins can be selectively eliminated. A needle is inserted into the vascular structure and the targeted abnormalities are subjected to emitted laser radiation. The device allows for orientation and positioning of the laser delivering optical fiber during treatment. An extension piece maintains the optical fiber in a fixed position relative to, and at a fixed distance from, a hand piece to allow the user to know the extent to which the fiber has been inserted into the vein.

U.S. Pat. No. 6,398,777 to Navarro et al. describes another ELA procedure in which percutaneous access into the vein lumen is obtained using an angiocatheter through which a fiber optic line is introduced. The fiber optic line has a bare, uncoated tip defining a flat radiation emitting face. The '777 patent teaches manually compressing the vein, such as by hand or with a compression bandage, to place the vein wall in contact with the flat emitting face of the fiber tip. The laser energy is delivered in high energy bursts into the portion of the vein wall in contact with the bare fiber tip. The wavelength of the laser energy is in the range from about 532 nm to about 1064 nm and the duration of each burst is about 0.2 seconds to about 10 seconds. Each burst delivers from about 5 watts to about 20 watts of energy into the vein wall. The '777 patent and other prior art ELA procedures teach delivering sufficient energy to insure damage to the entire thickness of the vein wall to ultimately result in fibrosis of the vein wall and occlusion of the greater Saphenous vein.

Consistent with the '777 patent, the prior art teaches applying relatively high energy levels (e.g., ≥80 J/cm) in order to improve the treatment success of ELA of incompetent Saphenous veins. Timperman et al. teach that endovenous laser treatments of the Saphenous vein are particularly successful when doses of more than 80 J/cm are delivered. Timperman et al. collected data regarding the length of treated vein and the total energy delivered on 111 treated veins. The wavelength of laser energy applied was 810 nm or 940 nm. Of the 11 treated veins, 85 remain closed (77.5%) during the follow-up period. In this group of successfully treated veins, the average energy delivered was 63.4 J/cm. For the 26 veins in the failure group, the average energy delivered was 46.6 J/cm. No treatment failures were identified in patients who received doses of 80 J/cm or more. P. Timperman, M. Sichlau, R. Ryu, "Greater Energy Delivery Improves Treatment Success Of Endovenous Laser Treatment Of Incompetent Saphenous Veins", Journal of Vascular and Interventional Radiology, Vol. 15, Issue 10, pp. 1061-1063 (2004).

One drawback associated with this and other prior art ELA treatments is that the laser radiation is applied only through the very small flat emitting face at the bare fiber tip. As a result, substantially only a very small, localized portion of the blood and/or vein wall in front of the flat emitting face directly receives the emitted laser energy at any one time. Yet another drawback of such prior art ELA devices and methods is that the laser radiation is directed only in a forward direction out of the flat emitting face of the fiber. Accordingly, substantially no radiation is emitted radially or laterally from the fiber tip thereby delivering the laser radiation in a relatively localized manner. A further drawback is that the relatively high levels of energy delivered into the vein create significantly increased temperatures which can, in turn, give rise to corresponding levels of pain in the surrounding tissues. The relatively high levels of energy delivered also can give rise to corresponding levels of thermal damage in surrounding tissues. The more intense the thermal damage, the greater is the chance for post procedure pain, bruising and the possibility of paresthesia. Paresthesia is an abnormal and/or unpleasant sensation resulting from nerve injury. Yet another drawback is that such relatively high levels of energy delivery and/or localized concentrations of laser radiation can give rise to vein perforations. As a consequence, such prior art ELA procedures can require relatively high levels of anesthetic, such a local tumescent anesthesia, more time, and can give rise to more stress to both a patient and physician, than otherwise desired.

A further drawback of prior art ELA treatments is that they employ a tumescent technique involving substantial volumes of tumescent anesthesia. For example, a typical prior art ELA treatment employs at least about 100 ml to about 300 ml or more of tumescent anesthesia depending on the length of vein to be treated. The tumescent anesthesia is injected into the tissue along the length of the vein. In some cases, the tumescent anesthesia is injected into a perivenous cavity defined by one or more fascial sheaths surrounding the vein. In other cases, the tumescent anesthesia is injected into the leg tissue surrounding the vein. Tumescent anesthesia typically consists essentially of dilute concentrations of Lidocaine and Epinephrine in a saline solution. One drawback of such tumescent techniques is that the anesthetic is toxic, and in some cases when, for example, substantial volumes are employed, the anesthetic can cause adverse patient reactions, such as convulsions. Yet another drawback of the tumescent technique is that patients can experience an undesirable elevation in blood pressure due to the use of Epinephrine. A still further drawback of the tumescent technique is that it requires the injection of substantial volumes of liquid anesthetic along the length of the vein, which adds a significant amount of time to the overall ELA procedure, and can give rise to adverse post treatment side effects, such as black and blue marks, and other adverse effects associated with such large volumes of anesthetic.

Although the tumescent anesthesia or cold saline tumescent infusion used in the tumescent technique of prior art ELA procedures creates a heat sink surrounding the vein, it can allow for significantly higher levels of thermal damage to the surrounding tissues than desired. The more intense the thermal damage the greater is the chance for post procedure pain, bruising, and the possibility of paresthesia. For example, the significant quantities of tumescent anesthesia employed in prior art ELA procedures typically will prevent a patient from feeling any thermal stimulation of the nerves, and therefore will prevent the patient from alerting the physician to stop or adjust the procedure to prevent undesirable thermal damage. The tibial nerve (TN) and its common peroneal nerve (CPN) branch both are subject to the possibility of such damage. The CPN is very superficial in the lateral leg just below the knee, and thermal damage to this nerve can lead to foot drop. Similarly, the TN is subject to the possibility of thermal damage when exploring high in the popliteal fossa. Depending on its extent, thermal damage to the TN can lead to muscle dysfunction of the calf and foot muscles. The sural nerve (SUN) and Saphenous nerve (SAN) likewise are subject to the possibility of thermal damage when performing ELA of the small Saphenous vein (SSV) or the GSV below the knee. The SUN runs very close to the SSV especially distally closer to the ankle. The SAN runs very close to the GSV below the knee especially, again, distally closer to the ankle. Significant quantities of anesthesia, such as tumescent anesthesia, can unknowingly lead to thermal damage of such nerves.

U.S. Pat. No. 6,986,766 relates to the application of markings on an optical fiber to determine fiber position relative to an introducer sheath. However, this and other related inventions lack information to determine pullback speed of a laser fiber while lasing. Slow uncontrolled pullback of the laser fiber or catheter can be cause for overheating and perforation of the vessel wall, as even the best surgeon may have difficulty retracting the fiber at exactly the correct speed to maintain an appropriate vessel wall heating temperature. On the other hand, excessive pullback speed may result in insufficient irradiated energy for proper vessel occlusion.

U.S. Patent Application No. 2004/0199151 to Neuberger, which is assigned to the Assignee of the present invention, and is hereby incorporated by reference in its entirety as part of the present disclosure, discloses a system and method for controllably releasing radiation in percutaneous radiation treatments. A laser is coupled to an optical fiber that is inserted below the skin or into a vascular lumen to a predetermined point. Radiation is then delivered to the treatment site while the fiber is simultaneously withdrawn toward the entry point. The fiber is manually withdrawn at a predetermined rate and radiation is administered in a constant power or energy level. To maintain a constant desired energy density, the speed of withdrawal is measured and sent to a controlling mechanism. The controlling mechanism modifies the power emitted, pulse length or pulse rate to ensure that the vein or tissue receives a consistent dose of energy. Although this is a considerable improvement over the prior art, the radiation is emitted through a flat emitting face located at the fiber tip and primarily in a longitudinal direction.

Accordingly, it is an object of the present invention to overcome one or more of the above-described drawbacks and/or disadvantages of the prior art.

SUMMARY OF THE INVENTION

The present invention provides an improved method and device for safe and efficient endoluminal laser ablation ("ELA") that may be performed at relatively low power densities.

In some embodiments, a device for endoluminal treatment of a blood vessel comprises a flexible waveguide defining an elongated axis, a proximal end optically connectable to a source of radiation, and a distal end receivable within the blood vessel. The distal end includes a radiation emitting surface that emits radiation from the radiation source laterally with respect to the elongated axis of the waveguide onto an angularly extending portion of the surrounding vessel wall.

In some embodiments, the device includes an emitting surface (or surfaces) that emits the laser energy radially and substantially circumferentially into the surrounding wall of the blood vessel and any blood, saline and/or other fluid located therebetween. In some embodiments the device emits pulsed or continuous laser energy radially through an optical fiber end with a substantially conical shaped emitting surface for 360° radial emission. Some embodiments of the device further include a substantially conical shaped reflective surface axially spaced relative to and facing the conical emitting surface for enhancing radial emission efficiency by reflecting radially and/or circumferentially remnant or designed forwardly transmitted energy.

In some embodiments, a plurality of grooves, notches or other means are axially spaced relative to each other along the fiber for causing radiation to be partially emitted radially outwardly of the fiber and partially transmitted to the subsequent groove or grooves. In some embodiments, the power density is maintained at a relatively low level, preferably about 10 W per cm$^2$ or lower. In other currently preferred embodiments, the emitting portion of the fiber defines a length within the range of about 1 cm to about 100 cm according to the length of vein to be treated.

In some embodiments, a method for endoluminal treatment of a blood vessel, comprises the following steps:
(i) introducing a waveguide defining an elongated axis into the blood vessel;
(ii) transmitting radiation through the waveguide; and
(iii) emitting radiation laterally with respect to the elongated axis of the waveguide onto an angularly extending portion of the surrounding vessel wall.

In some such embodiments, the emitting step includes laterally emitting radiation onto a region of the surrounding vessel wall extending throughout an angle of at least about 90°. In some embodiments, the emitting step includes laterally emitting radiation onto a region of the surrounding vessel wall extending throughout an angle within the range of about 90° to about 360°. Some embodiments further comprise the step of emitting radiation substantially radially with respect to the elongated axis of the waveguide in a substantially annular pattern onto the surrounding vessel wall. Some embodiments further comprise the step of reflecting forwardly emitted radiation laterally with respect to the elongated axis in a substantially annular pattern onto the surrounding vessel wall. Some embodiments further comprise the step of transmitting the radiation at a power of less then about 10 W at a wavelength within the range of about 980 nm to about 1900 nm.

In some embodiments, a method for endoluminal treatment of a blood vessel comprises the following steps:
(i) introducing an energy application device defining an elongated axis into the blood vessel;

(ii) maintaining the blood vessel at approximately the same size prior to and after introduction of the energy application device into the blood vessel;

(iii) applying energy from the energy application device laterally with respect to the elongated axis of the device into the surrounding wall of the blood vessel substantially without pre-shaping, flattening, compressing or moving the wall of the blood vessel toward the energy application device; and (iv) thermally damaging the blood vessel.

In some embodiments, a method for endoluminal treatment of a blood vessel comprises the following steps:

(i) introducing an energy application device defining an elongated axis into the blood vessel;

(ii) applying energy from the energy application device into the surrounding wall of the blood vessel substantially without pre-shaping, flattening, compressing or moving the wall of the blood vessel toward the energy application device;

(iii) substantially absorbing the applied energy within the wall of the blood vessel and causing sufficient damage to the intravascular endothelium to occlude the blood vessel; and (iv) substantially preventing transmission of the applied energy through the wall of the blood vessel and into tissue surrounding that blood vessel at a level that would thermally damage such tissue.

In some embodiments, the method further comprises the step of applying energy in the form of laser radiation at at least one substantially predetermined wavelength and at least one substantially predetermined energy delivery rate that causes the applied radiation to be substantially absorbed within the wall of the blood vessel to sufficiently damage the intravascular endothelium and occlude the blood vessel, and substantially prevents transmission of the applied radiation through the wall of the blood vessel and into the surrounding tissue at a level that would thermally damage such tissue.

In some embodiments, a method for endoluminal treatment of a blood vessel comprises the following steps:

(i) introducing an energy application device into the blood vessel;

(ii) delivering from the energy application device into a treatment area of the blood vessel a predetermined energy per unit length of blood vessel that on average is sufficiently high to close the blood vessel, but sufficiently low to substantially avoid the need for anesthetic along the treatment area; and (iii) thermally damaging and closing the blood vessel.

In some embodiments, a method for endoluminal treatment of varicose veins comprises the following steps:

(i) introducing an energy application device into the varicose vein;

(ii) delivering from the energy application device into a treatment area of the vein a predetermined energy per unit length of vein that is on average about 30 J/cm or less; and (iii) thermally damaging and closing the vein.

In some embodiments, the device includes a cap fixedly secured to a distal end of the fiber. In some such embodiments, the distal end of the fiber includes a flat emitting face and the cap encloses the emitting face. In other embodiments, the distal end of the fiber includes a radially-emitting surface, such as a conical surface, and a reflecting surface, and the cap encloses both emitting and reflective surfaces. In some embodiments, the cap is made of quartz or other radiation transparent material that is fused, bonded or otherwise fixedly secured to the fiber core for protecting the core and emitting surfaces thereof and transmitting the emitted and reflected radiation therethrough. In other embodiments, the cap is made of a relatively flexible, transparent material, such as polymeric Teflon AF, in order to achieve a relatively long, flexible emission zone. In the case of relatively low absorbed wavelengths, the cap can be made of an opaque material in order to transform all or part of the emitted energy into heat. In some embodiments the cap and/or fiber includes means for controlling the temperature within the vein and/or for regulating the power input and/or the pullback speed of the fiber.

One advantage of the subject devices and methods is that they can provide for a relatively fast, safe, efficient and/or reliable treatment in comparison to the above-described prior art treatments.

Another advantage of the currently preferred embodiments is that they allow for a substantially even and essentially uniform application of radiation at relatively low power densities to the vein wall, thereby minimizing the risk of perforating the vein wall and, in turn, reducing pain during and after the procedure in comparison to prior art treatments.

Yet another advantage of some currently preferred embodiments is that they allow for the safe and effective treatment of insufficient veins while avoiding the need for administration of general or local tumescent anesthesia. In some such embodiments, the need for anesthesia along the treated portion of the blood vessel is substantially avoided. In other embodiments, no general or local anesthetic, much less tumescent anesthetic, is needed at all.

A further advantage of some embodiments is that they provide a device and method for endovascular treatment by emitting radiation at multiple regularly-spaced emission points as well as extended diffuse radiation.

The above and other objects, features and advantages of the inventions disclosed herein and/or of the currently preferred embodiments thereof will become more readily apparent from the following detailed description read in conjunction with the accompanying drawings.

BRIEF DESCRIPTION OF THE DRAWINGS

FIG. 2b is a partial, side elevational view of the optical fiber of FIG. 2a.

FIG. 7b is a partial, cross-sectional view of the optical fiber tip of FIG. 7a.

DETAILED DESCRIPTION OF PREFERRED EMBODIMENTS

Figure 1A:
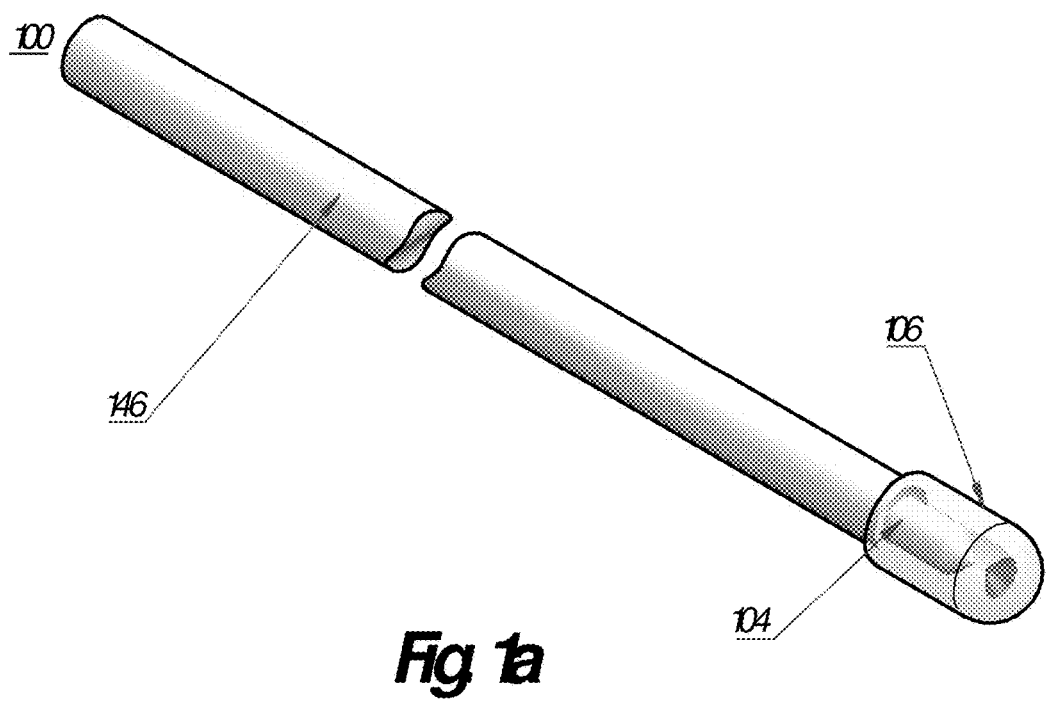
FIG. 1a is perspective view of a first embodiment of an optical fiber including a substantially conical shaped emitting surface on the tip of the optical fiber, a substantially conical shaped reflecting surface axially spaced relative to and facing the emitting surface, and a cap enclosing the emitting and reflective surfaces for achieving efficient 360° radial emission of the laser energy.

The currently preferred embodiments are hereinafter described with reference to the accompanying drawings wherein like reference numerals are used to indicate like elements throughout the various figures. As described further below, the currently preferred embodiments provide an improved method and device for safe and efficient low power density endoluminal treatment of venous insufficiency. Some currently preferred embodiments also provide radially emitting pulsed or continuous energy from an optical fiber. For circular irradiation, a conical or near conical fiber distal end is used with an opposing conical shaped reflective surface anchored in a cap distal region. In extended radial irradiation, multiple regularly or otherwise spaced emission grooves longitudinally positioned at the fiber's end can be used.

Another feature of some currently preferred embodiments is the possibility of achieving an extended emission zone. This can be done by appropriately arranging the sets of opposed conical shapes, through a combination of different variables, i.e., angle cut of conical surfaces, spacing between cones, refractive index of cap material, and gas composition left in the spacing. In addition, a series of graded lenses, such as a plurality of graded lenses axially spaced relative to each other, may be employed. Furthermore, slightly truncated conical tips also can be employed with proper allowances for the ray patterns formed in the spacing area. These variables can be adjusted to vary the width of the circular cross-section treated, as well as the distribution of power density across the spacing length. For example, if desired, a substantially uniform power density can be achieved across an entire irradiated cross-section.

Figure 1B:
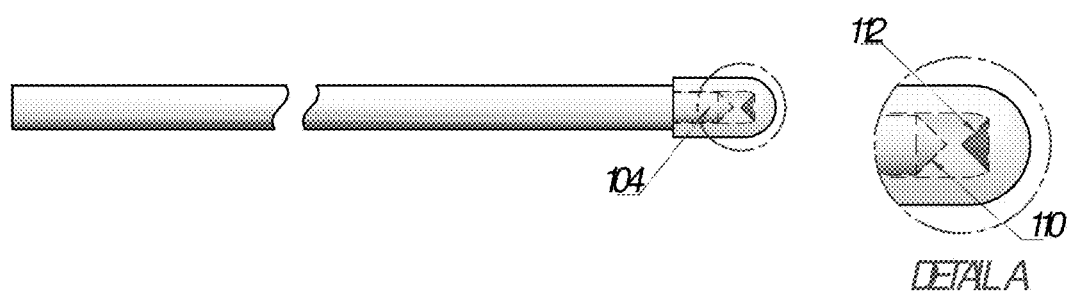
FIG. 1b is a partial, side elevational view of the optical fiber of FIG. 1a and an enlarged detail of the distal portion thereof.

As shown FIGS. 1a and 1b, a first embodiment of an optical fiber set is indicated generally by the reference numeral 100. The optical fiber 100 comprises a cladding 146, a core 140, and a quartz cap 106. An optical fiber tip preferably defines a substantially conical-shaped emitting surface 110 for achieving 360° radial emission. A preferably substantially conical-shaped reflective surface 112 is axially spaced relative to and faces the emitting surface 110 for enhancing efficiency and designed distribution within a zone of radial emission. As can be seen, the emitting and reflecting surfaces assembly is hermetically sealed within a quartz cap 106 that is fixedly secured to the end of the fiber and defines an air or other gas interface at the emitting surface to achieve radial/annular emission. Accordingly, due to the angle of the emitting surface 110 and the differences of the indices of refraction of the emitting face 110 and air or other gas interface provided within the sealed cap 106, the laser radiation is emitted radially (i.e., transverse to or laterally with respect to the elongated axis of the fiber) and annularly from the fiber directly onto the surrounding vessel wall. Preferably, the emitting surface 110 is oriented at an acute angle with respect to the elongated axis of the fiber that is set for substantially total refraction of the emitting radiation laterally with respect to the elongated axis of the fiber. In some embodiments, the radiation is emitted laterally and annularly onto the surrounding vessel wall, and the annular beam of radiation extends throughout an arc (i.e., the spread of the beam) defined by the numerical aperture of the fiber. In some embodiments, the spread of the annular beam is defined by an angle within the range of about 30° to about 40°. In addition, the approximate center of the beam is preferably oriented at an angle within the range of about 70° to about 90° relative to the elongated axis of the fiber.

One advantage of this novel configuration is that substantially all radiation is radially emitted, and therefore it significantly enhances radial emission efficiency in comparison to the above-described prior art. A laterally or radially emitted annular beam can define substantially less volume than an axially or forwardly directed conical-shaped beam as emitted, for example, by a flat, bare tipped fiber, and therefore the laterally emitted beam can more directly and efficiently transmit radiation into a vessel wall. In addition, the emitting characteristics can be adjusted to vary the length of the annular area of the blood vessel or other hollow anatomical structure treated, as well as the distribution of power density along the length of such annular section. For example, in another embodiment, a multi-grooved distal fiber end, defining a linear distribution of axially spaced grooves, may be used to irradiate an extended linear arc sector of the vein wall to, in turn, allow for effective relatively low power density treatment. In a preferred embodiment, the fiber, with a linearly distributed multi-grooved distal end, is rocked back and forth or rotated (e.g., about one revolution) during irradiation to achieve 360° radial stimulation of the vein wall. Alternatively, the grooves can be offset about the fiber to provide a roughly circular pattern with either pullback or revolving motions.

Figure 2A:
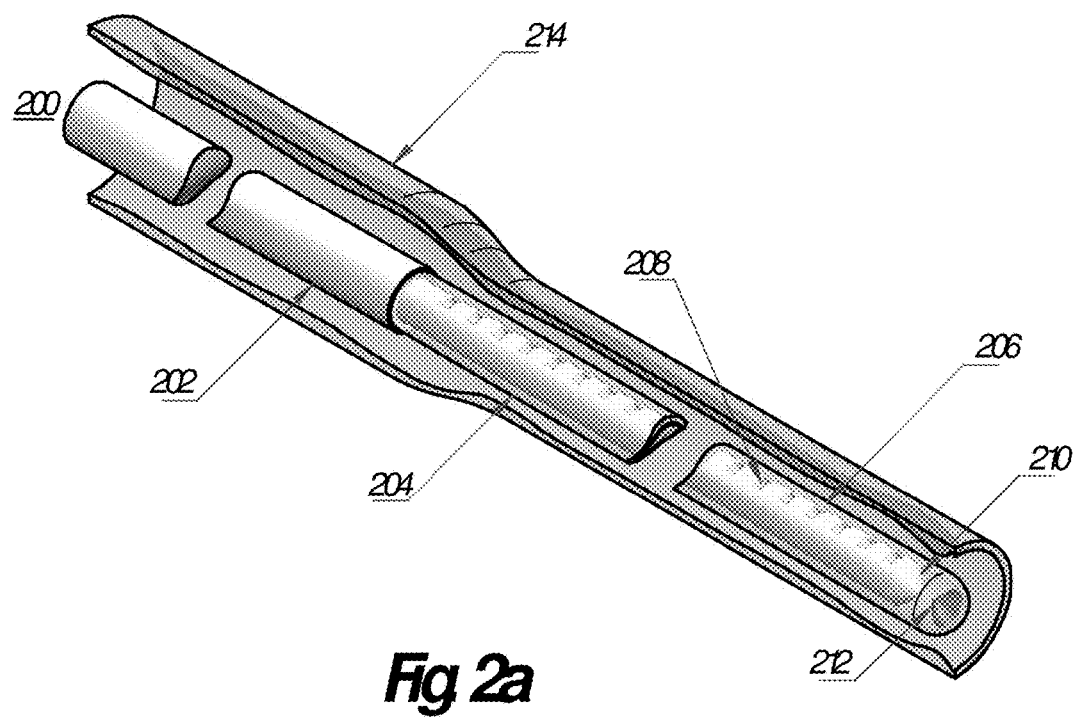
FIG. 2a is a partial, perspective view of another embodiment of an optical fiber received within a blood vessel.
Figure 2B:
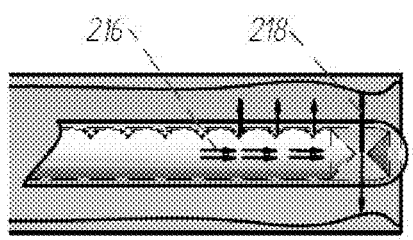
Figure 2C:
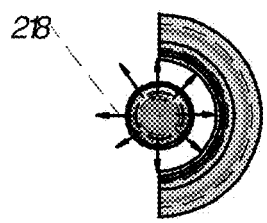
FIG. 2c is an end elevational view of the optical fiber of FIG. 2a with part of the blood vessel removed for clarity.

Turning to FIGS. 2a, 2b and 2c, another embodiment of an optical fiber is indicated generally by the reference numeral 200. The optical fiber 200 comprises a normal section 202 extending along the majority of its length from the proximal end, which is optically connected to a laser source, to a laser radiation emitting distal end section 204. The emitting section 204 comprises several regularly-spaced grooves, preferably spaced about 1 mm to several mm apart, for achieving radial laser emission 218 along an emission zone. Each groove 208 causes some radiation to be partially emitted radially outwardly of the fiber 218 and the remaining radiation 216 partially transmitted to a subsequent groove 208.

The optical fiber tip 210 may define a substantially conical shape for achieving 360° radial emission and placed opposite to it, there is a preferably conical reflective surface 212 which, as explained previously, enhances efficiency and distribution of 360° radial emission by reflecting out any remnant or designed forwardly transmitted energy in 360° radial directions.

The emission section 204 of the fiber 200 is covered by a protective cap 206. In one preferred embodiment, when the wavelength used is highly absorbed in the target tissue 214, the protective cap 206 is made of quartz or other radiation transparent or substantially radiation transparent material (i.e., a material that permits transmission of the radiation or a substantial portion thereof therethrough), such as polymeric Teflon AF, in order to achieve a relatively long, flexible emission zone. In another preferred embodiment, when the wavelength used is poorly absorbed in the target tissue 214, the protective cap 206 is made of a radiation opaque material (i.e., a material that absorbs the emitted radiation) in order to transform substantially all or part of the radially emitted radiation into heat in order to thermally damage the vein wall. This achieves vein collapse by thermal means instead of direct laser radiation.

Figure 3:
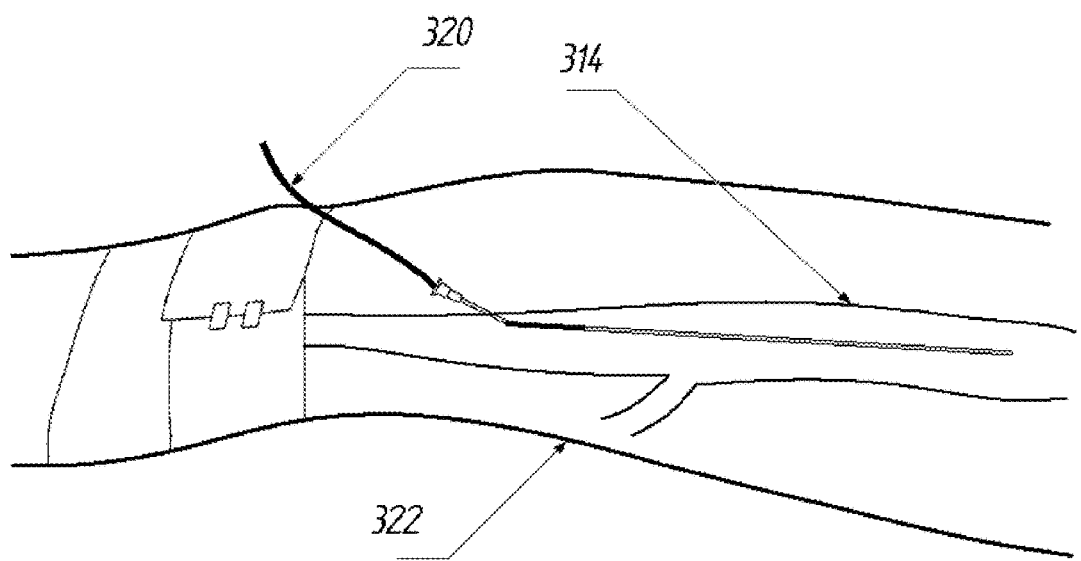
FIG. 3 is a somewhat schematic illustration of the optical fiber of FIG. 1 or 2 placed within a vein to be treated.

Turning to FIG. 3, another embodiment of an optical fiber is indicated generally by the reference numeral 320 and is shown placed at a pre-determined position within a vein 314. It can be appreciated from this figure that due to the relatively long emission zone of the optical fiber 320, a large portion of the vein can be treated at each position (e.g., the vein may be segmentally ablated). The fiber emission section length can be any desired length, including without limitation, a length within the range of about 1 cm to about 100 cm, within the range of about 1 cm to about 75 cm, or within the range of about 1 cm to about 50 cm. In a particular case in which the emission section length coincides with the total length of the vein section to be treated, a shorter and simpler treatment may result, as controlled pullback may be no longer necessary. In one such embodiment, the entire diseased length may be treated at once with the fiber pulled back as the vein wall collapses. In other embodiments, the grooves are sufficiently spaced (e.g., within the range of about ½ cm to about 2 cm apart, and in one embodiment, about 1 cm apart), and extend along a sufficient length of the fiber, to treat the entire blood vessel, or a desired portion thereof, with the fiber substantially maintained in place and without pullback thereof. In other embodiments, the blood vessel is segmentally ablated by treating extended sections of the blood vessel in sequence. In one such embodiment, the fiber is held in place within a first section of the blood vessel and the laser is fired to treat the first section, the laser is then turned off and the fiber is pulled back and placed in a second section of the vessel, the fiber is then held in place in the second section of the vessel while the laser is fired to treat the second section, and these steps are repeated to treat any additional sections of the blood vessel as required. In other embodiments, the laser is not turned off during fiber pullback or movement from one vein segment to another. In other embodiments, the fiber is held stationary while lasing in some sections of the blood vessel, and is pulled back while lasing in other sections of the blood vessel.

Figure 4:
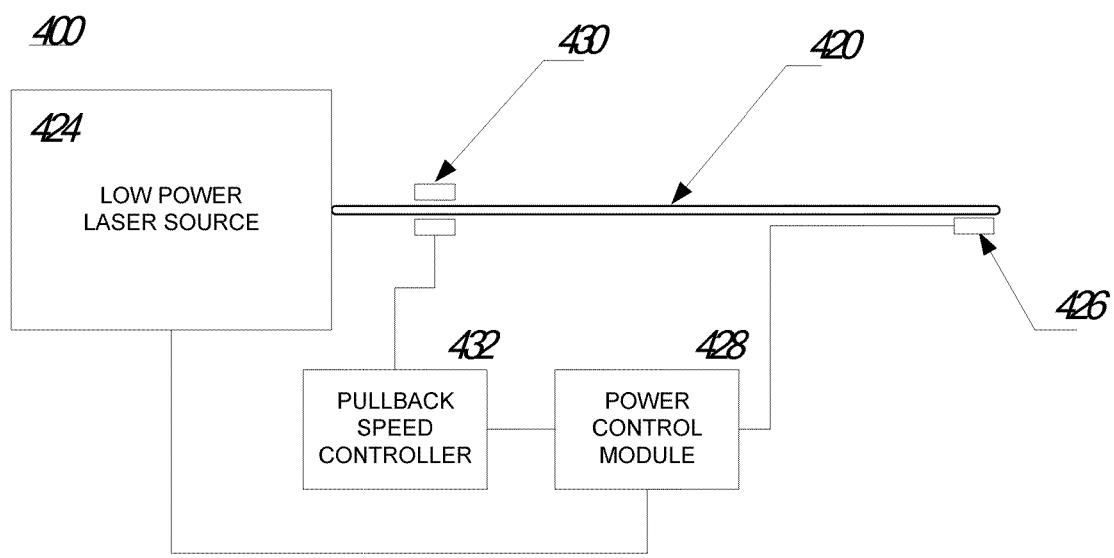
FIG. 4 is a schematic diagram of a preferred embodiment of a device including a laser radiation source, an optical fiber, a temperature sensor, a power control module, and a pullback actuator that is controlled by a pullback speed controller.

As shown in FIG. 4, another embodiment of an ELA system comprises a laser radiation source 424, an optical fiber 420, a temperature sensor 426, a power control module 428, and a pullback actuator 430 driven by a pullback speed controller 432. While lasing, the power control module 428 receives temperature values from the temperature sensor 426, preferably a thermocouple, positioned near the target tissue. In one embodiment, the temperature sensor is mounted on the fiber or cap proximate to the emitting/reflecting surfaces thereof. The power control module 428 processes information received from the temperature sensor 426 and provides feedback to both the laser power source 424 and the pullback speed controller 432. In one embodiment, the power control module 428 calculates the ideal or otherwise desired power density and pullback speed, and sends this information respectively to the laser power controller 428 and pull back speed controller 432. The pull back speed controller 432 controls the pullback actuator 430 to withdraw the fiber through the blood vessel, and the laser radiation source 424 sets the laser power in accordance with the control signals received from the control module 428. One advantage of these embodiments is that the power density and/or pull back speed of the optical fiber can be adjusted throughout the endoluminal treatment procedure to, for example, ensure vein closure while substantially preventing localized hot spots that otherwise might give rise to vein wall perforations, or substantially preventing overheating of the vein and/or surrounding tissues that would otherwise unnecessarily cause pain or discomfort for the patient. In another embodiment, with manual pullback, the power control module 428 suggests to the physician the ideal or desired power density and pullback speed values by showing them on a display, allowing more efficient and effective manual pullback. The system and/or components thereof for monitoring temperature and controlling pullback speed and other system variables may be manufactured and used in accordance with the teachings of commonly assigned U.S. patent application Ser. No. 11/900,248, filed 11 Sep. 2007, entitled "Vein Treatment Device And Method", and U.S. patent application Ser. No. 11/443,143, filed 30 May 2006, entitled "Power Regulated Medical Underskin Irradiation", each of which is hereby expressly incorporated by reference in its entirety as part of the present disclosure.

In some currently preferred embodiments, a low power density is applied, for example about 10 $W/cm^2$ or lower, while sufficiently high total energies can be applied to the vein in a reasonably short time to assure collagen denaturation, shrinkage and elimination of the vein. This can be enhanced by the extended emitting zone (or section) and the 360° radial irradiation such that during pullback, areas first irradiated by the proximal side of the emitting zone continue to receive irradiation from the center and distal side of the emitting zone.

Figure 5:
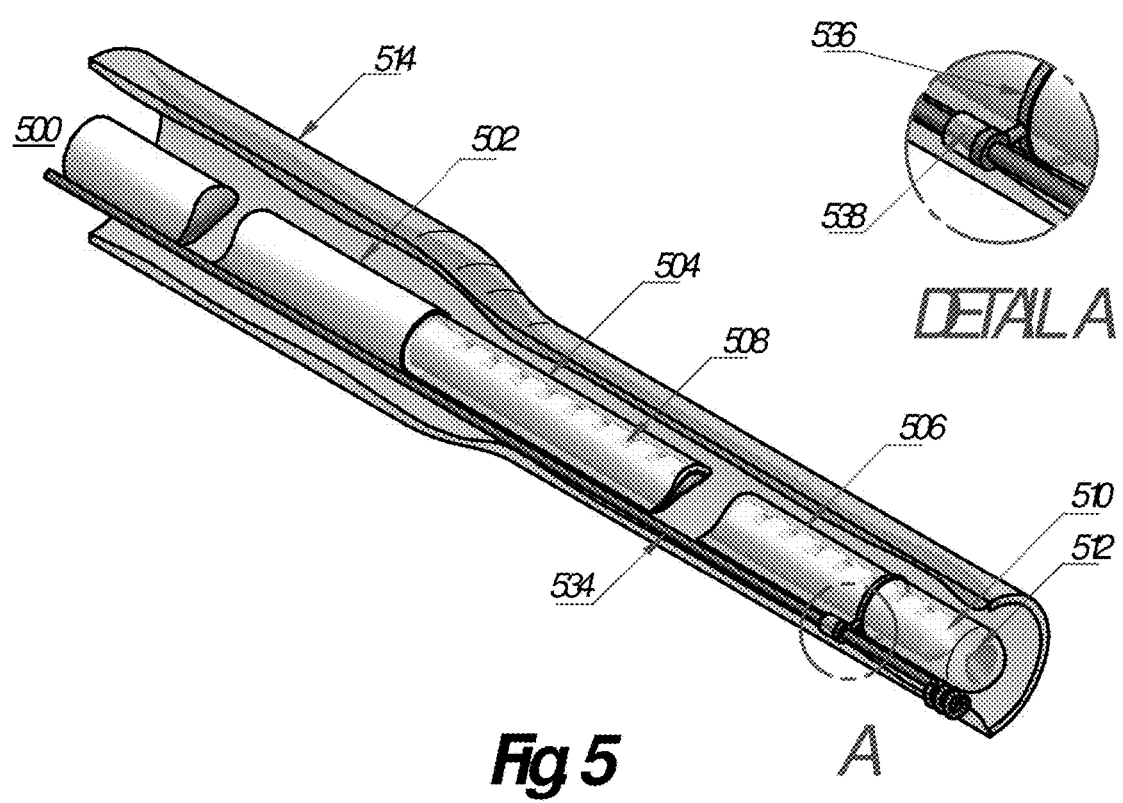
FIG. 5 is a partial, perspective view of another embodiment of an optical fiber including a protective quartz cap, an optical fiber distal end core with superficial grooves, a reflective surface, and a guide wire attached to the distal end of the fiber and extending distally therefrom, and an enlarged detail of the attachment of the guide wire to the cap.

Turning to FIG. 5, another embodiment of an optical fiber is indicated generally by the reference numeral 500. The optical fiber 500 comprises a normal section 502 for the majority of its length extending from the proximal end, which is optically connected to the laser source, to a laser radiation emitting distal section 504. The emitting section 504 comprises several regularly or otherwise spaced grooves for achieving radial laser emission along the emission zone. The optical fiber tip 510 defines a standard critical angle distal end, but preferably defines the illustrated conical shape for achieving 360° radial emission, and includes a conical reflective surface 512 axially spaced relative to and oppositely facing the emitting surface for enhancing efficiency and effectiveness of radial emission by reflecting out any designed or remnant forwardly transmitted energy in radial directions.

A guide wire 534 is attached to the quartz cap 506 by a mechanical guide wire attachment/detachment system 536. While inserting the treatment set into a blood vessel 514, the guide wire 534 remains attached to the optical fiber, due to its illustrated configuration. At the attachment site, the guide wire 534 is appropriately shaped at 538, so that the attachment system 536 prevents disengagement while pushing inwardly but allows detachment while pulling backwardly, thus allowing its extraction prior to or at the start of the treatment. In another embodiment, the guide wire is attached by means of a medically safe adhesive, e.g., a wax orcyanoacrylate. As may be recognized by those of ordinary skill in the pertinent art based on the teachings herein, the guide wire may be attached in any of numerous different ways, including with any of numerous different adhesives or other attachment mechanisms, that are currently known, or that later become known. The guide wire can be detached, post proper positioning of the treatment set inside the blood vessel, by means of the laser radiation, which softens the adhesive or degrades the adhesive bonding. Once detached, the guide wire 534 is removed, leaving the capped optical fiber 500 in the proper position and prepared for lasing. While lasing, the optical fiber is withdrawn in the direction toward the insertion site, shrinking the blood vessel 514 and preferably occluding the vessel.

Figure 6:
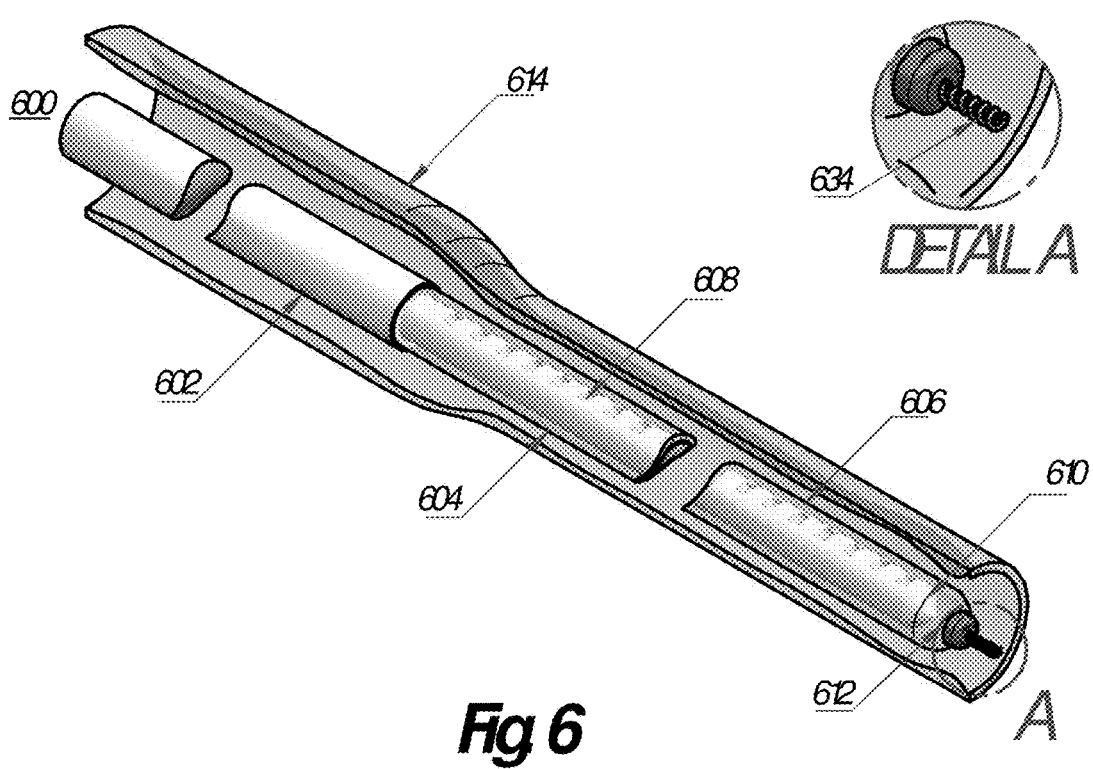
FIG. 6 is a partial, perspective view of another embodiment of an optical fiber comprising an optical fiber set with a guide wire attached to the distal end of a quartz protective cap.

In another preferred embodiment, depicted in FIG. 6, the optical fiber set 600 comprises an optical fiber, a quartz cap 606 and a guide wire 634. Radial laser emission is accomplished through a plurality of superficial grooves 608 with reflective surfaces 610 formed at the distal end section of the fiber optical core. In this case, the guide wire 634 is preferably attached to the distal end of the cap 606. Thus, the optical fiber set 600 can be easily introduced and guided through a blood vessel 614 to the desired position in a single step, without the need to remove the guide wire 634. Once in appropriate position, the physician starts lasing while withdrawing the optical fiber set 600 toward the insertion site, thereby shrinking the blood vessel 614 preferably to closure.

Figure 7A:
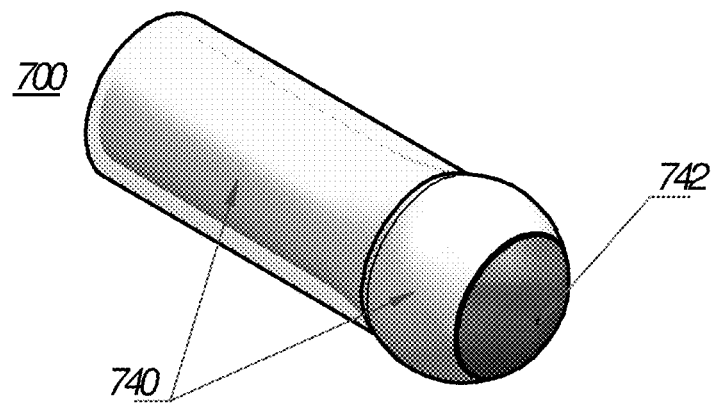
FIG. 7a is a partial, perspective view of another embodiment of an optical fiber wherein the optical fiber tip defines a reflective cone.
Figure 7B:
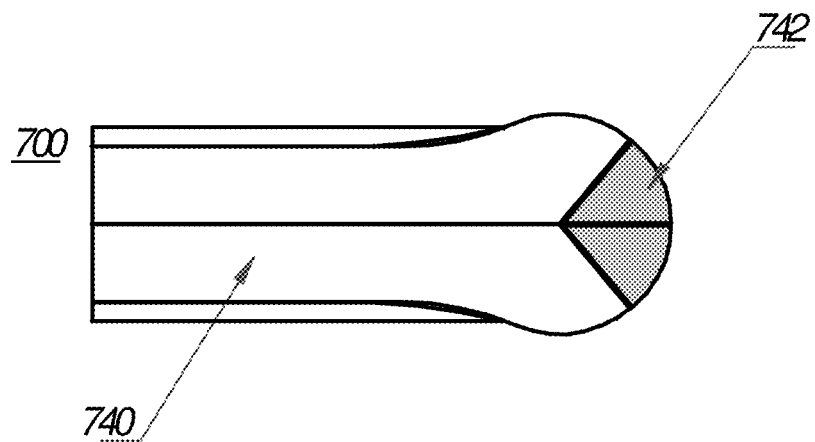

In FIGS. 7a and 7b, another embodiment of an optical fiber is indicated generally by the reference numeral 700. The optical fiber 700 achieves radial emission by means of a reflective cone 742 placed at the optical fiber tip 700. In this embodiment, the reflective cone 742 is defined by a concave, substantially conical shaped surface. Accordingly, radiation transmitted through the fiber core 740 is radially emitted over 360° when it reaches the fiber tip. Preferably, the concave, substantially conical shaped surface of the cone 742 defines an acute angle with respect to the elongated axis of the fiber that is within the range of about 30° to about 50°. As with the other embodiments described above, one advantage of this novel concave, conical shape, is that it achieves efficient 360° radial emission onto a surrounding vessel wall.

Figure 8A:
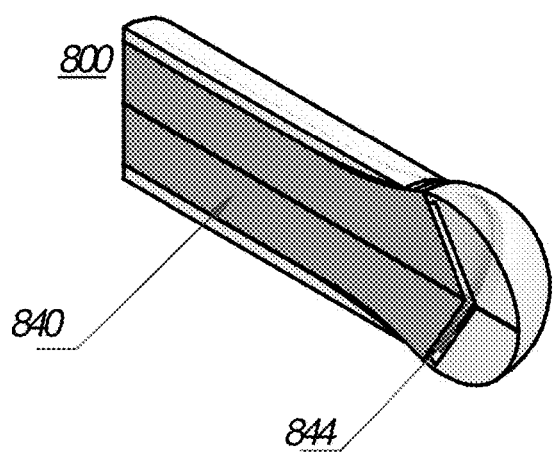
FIG. 8a is a partial, perspective, cross-sectional view of another embodiment of an optical fiber including an optical fiber tip with a reflective gap.
Figure 8B:
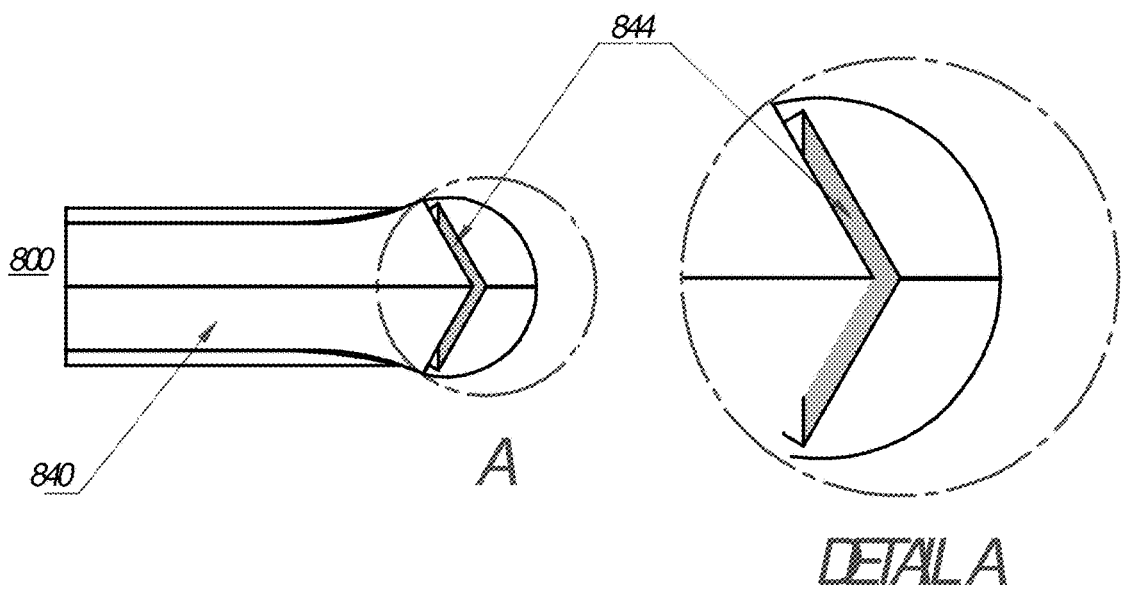
FIG. 8b is a cross-sectional view of the optical fiber tip of FIG. 8a and an enlarged detail thereof.

In FIGS. 8a and 8b, another embodiment of an optical fiber is indicated generally by the reference numeral 800. The optical fiber 800 achieves radial emission by means of a conically-shaped reflective gap formed at the optical fiber tip. As can be seen, the gap 844 is defined by convex, substantially conical-shaped emitting surface formed at the distal end of the fiber core 840, and a concave, substantially conical-shaped surface that is substantially transparent to the emitted radiation and is axially spaced relative to the emitting surface to form the gap 844 therebetween. In this embodiment, radiation transmitted through the fiber core 840 is radially emitted when it reaches the fiber tip due to the difference in refraction properties between the air or other gas within the gap 844 and fiber core 840. Accordingly, the radiation is radially emitted (i.e., in a lateral direction with respect to the elongated axis of the fiber) in an annular or circumferential pattern onto an adjacent surrounding vessel wall. This diffuser tip configuration leads to efficient 360° radial emission. As can be seen, a relatively thin wall is formed between the outer periphery of the gap 844 and the exterior of the fiber 800 to seal the gap within the fiber tip and thus maintain the requisite core-gas interface at the gap for annular radial laser emission. As with the other embodiments described herein, this novel configuration leads to efficient radial emission onto the surrounding vessel wall. As can be seen, the distal tip of the fiber 800 defines an expanded diameter or bulbous portion, which in the illustrated embodiment is substantially hemispherical shaped, to facilitate movement of the tip through a blood vessel. As may be recognized by those of ordinary skill in the pertinent art based on the teachings herein, although the bulbous portion is hemispherical shaped, it may take any of numerous different bulbous or like shapes and/or configurations that are currently known, or that later become known.

Figure 9:
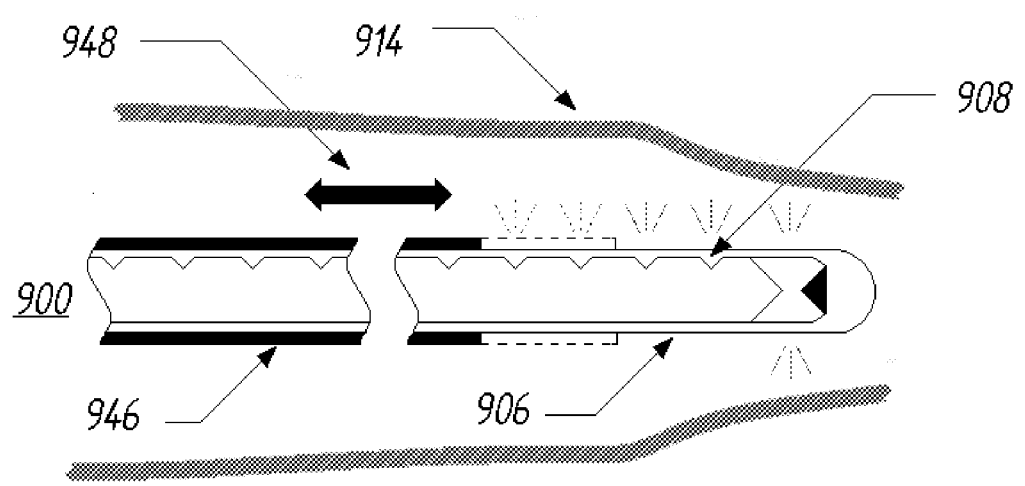
FIG. 9 is a partial, cross-sectional view of another embodiment of an optical fiber including an external sleeve slidably mounted over the fiber and/or cap that defines an internal reflective surface for preventing the transmission of laser radiation therethrough and for controlling the length of the emitting section of the fiber.

In another embodiment illustrated in FIG. 9, the cap 906 of the fiber 900 is partially covered by a sleeve 946 of radiation reflective material. As indicated by the arrows in FIG. 9, the sleeve 946 can be shifted axially relative to the cap 906 and fiber 900 to control the axial length of the emitting portion of the fiber. As can be seen, the sleeve 946 can be set to completely cover a desired number of radially emitting grooves 908, or some portion or all of the distal emitting section. Accordingly, one advantage of the embodiment of FIG. 9 is that is permits a physician to regulate the length of the emitting section or portion of the fiber. In one embodiment, the length of the emitting portion is set according to the length of the vessel 914 or section thereof to be treated to segmentally ablate such section(s). In another embodiment, the extended emitting section is pulled back through the vein while lasing to progressively lase one or more treated portions of the vein with substantially the entire extended emitting section. When the vein portion is shorter than the emitting fiber length, the sleeve may be used to cover the emission portion that is located outside of the vein while lasing. The sleeve is preferably made of a reflective material of a type known to those of ordinary skill in the pertinent art for performing this function. Even with perfect mirrored surfaces, the reflected light will pass back through the fiber such that some portion of the radiation will be captured, some scattered and some absorbed. Accordingly, a certain amount of the energy emitted at the grooves covered by the sleeve is lost as heat. Nevertheless, as the power density involved is low, any such heat build up can be maintained within an acceptable minimum value during an ELA treatment.

Figure 10:
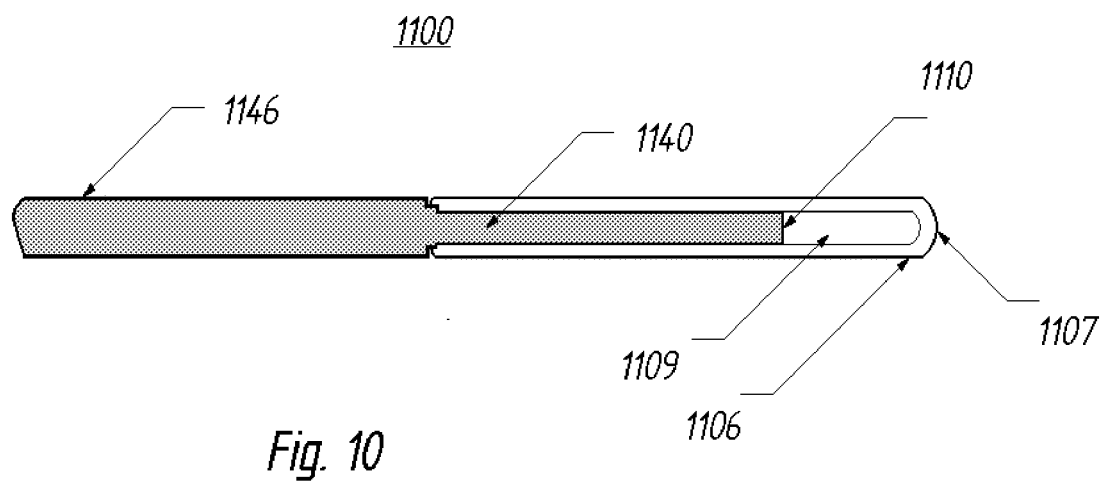
FIG. 10 is a partial, cross-sectional view of another embodiment of an optical fiber including a substantially flat emitting face sealed within a protective, radiation transparent cap.

Turning to FIG. 10, another embodiment of an optical fiber is indicated generally by the reference number 1100. The optical fiber 1100 is substantially similar to the optical fiber 100 described above with reference to FIGS. 1a and 1b, and therefore like reference numerals preceded by the numeral "11" instead of the numeral "1" are used to indicate like elements. The primary difference of the optical fiber 1100 in comparison to the optical fiber 100 is that the optical fiber tip defines a substantially flat emitting face 1110 that is sealed within the protective a cap 1106. The cap 1106 is made of a material that is substantially transparent to the emitted radiation to allow the radiation to pass through it and into the vessel wall. In one embodiment, the cap 1106 is made of quartz and is adhesively bonded to the fiber core as described above; however, if desired the cap may be made of any of numerous different materials, and may be fixedly secured to the distal end of the fiber in any of numerous different ways, that are currently known, or that later become known. As can be seen, the protective cap 1106 extends distally relative to the flat emitting face 1110 of the fiber, and defines a distal end 1107 that is rounded to facilitate movement of the capped fiber through a tortuous blood vessel. The distal end 1107 of the cap 1106 extends distally relative to the flat emitting face 1110 of the fiber an axial distance that is preferably within the range of about 2 to about 6 times the diameter of the fiber core, and more preferably within the range of about 3 to about 5 times the diameter of the fiber core. In the illustrated embodiment, the distal end 1107 of the cap 1106 extends distally relative to the flat emitting face 1110 of the fiber an axial distance that is about 4 times the diameter of the fiber core. As can be seen, the protective cap 1106 defines an enclosed space 1109 extending between the flat emitting face 1110 and the distal end 1107 of the cap that allows the transmitted radiation to pass through the space and the wall of the cap, but prevents any contact between the flat emitting face and the blood vessel wall and otherwise protects the emitting face of the fiber. In contrast to the optical fiber 100 described above, the optical fiber 1100 does not define a substantially conical-shaped emitting surface or a substantially conical-shaped reflective surface. Thus, the optical fiber 1100 emits a substantially conical-shaped beam forwardly or in the axial direction of the fiber.

Figure 11:
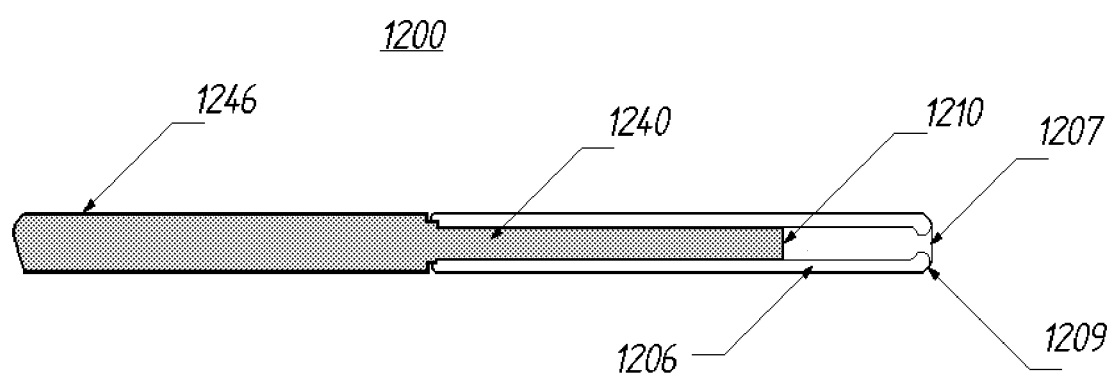
FIG. 11 is a partial, cross-sectional view of another embodiment of an optical fiber including a substantially flat emitting face sealed within a protective, radiation transparent sleeve.

Turning to FIG. 11, another embodiment of an optical fiber is indicated generally by the reference number 1200. The optical fiber 1200 is substantially similar to the optical fiber 1100 described above in connection with FIG. 10, and therefore like reference numerals preceded by the numeral "12" instead of the numeral "11" are used to indicate like elements. The primary difference of the optical fiber 1200 in comparison to the optical fiber 1100 is that the fiber 1200 includes an open protective sleeve 1206 rather than a closed protective cap. The protective sleeve 1206 is made of a material that is substantially transparent to the emitted radiation to allow the radiation to pass through it and into the vessel wall. In one embodiment, the protective sleeve 1206 is made of quartz and is adhesively bonded to the fiber core in substantially the same manner as is the protective cap described above; however, if desired, the protective sleeve may be made of any of numerous different materials, and may be fixedly secured to the distal end of the fiber in any of numerous different ways, that are currently known, or that later become known. As can be seen, the protective sleeve 1206 extends distally relative to the flat emitting face 1210 of the fiber, and defines a distal end 1207 that is rounded or curved inwardly toward a central aperture 1209. The distal end 1207 is curved inwardly in order to facilitate movement of the fiber tip through a blood vessel. The protective sleeve 1207 extends distally relative to the flat emitting face 1210 of the fiber an axial distance that is preferably within the range of about 2 to about 6 times the diameter of the fiber core, and more preferably within the range of about 3 to about 5 times the diameter of the fiber core. In the illustrated embodiment, the protective sleeve 1207 extends distally relative to the flat emitting face 1210 of the fiber an axial distance that is about 4 times the diameter of the fiber core. In contrast to the optical fiber 100 described above, the optical fiber 1200 does not define a substantially conical-shaped emitting surface or a substantially conical-shaped reflective surface. Thus, the optical fiber 1200 emits a substantially conical-shaped beam forwardly or in the axial direction of the fiber.

In the operation of the currently preferred embodiments, the optical fiber or other waveguide is first introduced into the vein to be treated. A local infiltration anesthetic, such as 0.5% dilute Lidocaine (preferably without Epinephrine) may be introduced at the access site, if needed. In one embodiment, about ½ ml of such local anesthetic is used at the access site. An introducer needle is inserted through the access site and into the vein to gain access to the vein. A guide wire then may be introduced through the introducer needle and into the vein. Then, an introducer sheath may be introduced over the guide wire into the vein. The introducer sheath may take the form of any of numerous different introducer sheaths that are currently known, or that later become known, including a short introducer sheath that provides access to a relatively short portion of the vein adjacent to the access site (e.g., defining a length of less than about 11 cm, or within the range of about 6 cm to about 11 cm) or a longer introducer sheath that can extend up the length of the vein to be treated. The guide wire is then removed through the sheath. Then, the optical fiber is introduced through the introducer sheath until the emitting tip of the fiber is positioned about 1½ cm or other desired distance below the sapheno-femoral junction ("SFJ"). The fiber tip is positioned at the appropriate start point below the SFJ under ultrasound guidance and/or by transmitting a red or other noticeable aiming beam through the fiber to visually monitor the start position of the fiber tip through the skin.

One advantage of the currently preferred embodiments is that the cap or other distal portion of the fiber tip is rounded, thus facilitating ease of insertion through a tortuous vein and eliminating the need, in many, if not all instances, for an introducer sheath and guide wire. In the currently preferred embodiments, the fibers define an outer diameter within the range of about 1235 μm to about 1365 μm, the caps define an outer diameter within the range of about 1800 μm to about 2000 μm, and the rounded distal portion of the cap is defined by a radius within the range of about 900 μm to about 1000 μm. Accordingly, although the use of an introducer sheath and guide wire is described above, such steps may be eliminated. Alternatively, if an introducer sheath is used, it may be removed from the vein prior to lasing and pullback of the fiber. For example, if a long introducer sheath is used, the introducer sheath may be pulled back and out of the vein prior to lasing and pullback of the fiber. Similarly, if a tear-away introducer sheath is used, the sheath may be torn away and removed from the vein prior to lasing and pullback of the fiber. If a relatively short introducer sheath is used, the sheath may be removed from the vein, or held in place at the access site during lasing and pullback.

With the fiber tip at the start position immediately below the SFJ or other desired start position, the laser is actuated to emit laser energy into the blood vessel. With the radial-emitting fibers, the laser energy is directed preferably radially and annularly onto the surrounding wall of the blood vessel. With the flat-tipped fibers, on the other hand, the laser energy is emitting in a substantially conical, axially directed beam. As the radiation is emitted, the fiber is pulled back at a substantially predetermined rate based on the wavelength and power used to damage or kill a sufficient portion of the intravascular endothelium to achieve vessel closure. Preferably, the energy per unit length delivered to the blood vessel is sufficiently high to close the vein, but sufficiently low to substantially avoid the need for anesthetic along the treated length of the vessel. In the currently preferred embodiments, the energy per unit length delivered to a treatment area of a blood vessel is on average less than 80 J/cm, preferably less than about 50 J/cm, more preferably less than about 40 J/cm, more preferably less than about 30 J/cm, more preferably less than about 20 J/cm, and even more preferably less than about 10 J/cm. In some embodiments, the energy per unit length delivered to a treatment area of a blood vessel is on average within the range of about 3 J/cm to about 15 J/cm, and preferably is within the range of about 5 J/cm to about 10 J/cm. In these embodiments, and as described further below, the wavelength of the radiation is preferably relatively strongly absorbed in water and relatively weakly absorbed in hemoglobin or oxyhemoglobin (e.g., ≥ to about 1064 nm). One advantage of such predetermined energy levels and/or wavelengths is that (i) the energy may be substantially entirely absorbed within the wall of the blood vessel, (ii) the intravascular endothelium is sufficiently damaged to achieve vessel closure, and (iii) the transmission of any significant radiation into the tissues surrounding the blood vessel is substantially prevented to thereby substantially avoid the need for an anesthetic along the treated portion of the vessel.

Also in the currently preferred embodiments, the energy, such as laser radiation, may be applied in a continuous mode, or in a pulsed mode. It has been discovered that the delivery of energy in a pulsed mode may allow for the delivery on average of higher levels of energy per unit length to a treatment area of a blood vessel substantially without the application of an anesthetic to such treatment area, in comparison to the delivery of laser energy in a continuous mode (i.e., higher amounts of pulsed energy may be absorbed within the vessel in comparison to continuous mode energy, while substantially preventing transmission of any significant energy through the vessel wall that otherwise would thermally damage surrounding tissue). In addition, as a general matter, and all other factors being equal, in a pulsed mode, the greater the percentage that the duty cycle is "off" as opposed to "on", the higher may be the energy per unit length delivered on average to a treatment area of a blood vessel, substantially without requiring administration of an anesthetic along such treatment area. In some such embodiments, more than about ½ of the duty cycle is "off", and preferably about ½ to about ⅔ of the duty cycle is off. Pulsing can significantly increase the rate of decay of the radiation within the vessel wall tissue in comparison to continuous mode delivery, thereby resulting in a lower depth of penetration per given energy delivery rate (e.g., the J/cm delivered on average by the intravascular energy delivery device) than without pulsing (e.g., continuous mode). Accordingly, one advantage of delivering energy in a pulsed mode is that it allows for a higher energy delivery rate, and thus may allow for a higher amount of energy to be delivered to the intravascular endothelium, without the use of an anesthetic along the treated portion of the vessel. The term "pulsed mode" is used herein to mean any of numerous different ways that are currently known, or that later become known, for subjecting the energy delivered to the blood vessel to a duty cycle (i.e., a recurring period, a fraction of which the energy delivery is active, and another fraction of which the energy delivery is inactive), such as a laser radiation duty cycle, including without limitation pulsing, repeatedly turning the energy source on and off, and interrupting an energy beam, such as with a shutter.

In some currently preferred embodiments, the wavelength of the radiation is about 1470 nm, ±about 30 nm. In other preferred embodiments, the wavelength of the radiation is about 1950 nm, ±about 30 nm. Other embodiments employ radiation at about 810 nm, about 940 nm, about 1064 nm, about 1320 nm, about 2100 nm, about 3000 nm, and about 10,000 nm, each ±about 30 nm. One advantage of wavelengths that are significantly more highly absorbed in water than in hemoglobin or oxyhemoglobin, is that such wavelengths are not strongly absorbed in blood but are strongly absorbed in blood vessel tissue. Accordingly, such wavelengths tend to substantially pass through intervening blood between the emitting surface(s) of the fiber and the vessel wall and, in turn, are strongly absorbed in the vessel wall. Such wavelengths delivered below a predetermined energy delivery rate are substantially entirely absorbed within the blood vessel wall tissue to, in turn, damage or kill a sufficient depth of intravascular endothelium to facilitate blood vessel closure. Preferably, such damage to the intravascular endothelium is at a level on average of at least about ⅓ the thickness of the intravascular endothelium, or is on average within the range of about ⅓ to about ⅔ the thickness of the intravascular endothelium. As a result, such wavelengths can be more readily absorbed at relatively low predetermined energy delivery rates (e.g., less than about 50 J/cm delivered on average to the treatment section of the blood vessel, preferably less than about 40 J/cm, more preferably less than about 30 J/cm, more preferably less than about 20 J/cm, and even more preferably less than about 10 J/cm) that nevertheless are sufficient to damage or kill a sufficient depth of intravascular endothelium to facilitate blood vessel closure. In addition, because such radiation is substantially entirely absorbed within the blood vessel wall, any heating of tissues that are near or adjacent to the vessel wall is substantially prevented, and thus the procedure can be performed substantially without anesthetic about the treated portion of the blood vessel (e.g., a local non-tumescent anesthetic may be applied at the access site only, or otherwise only at one or a few discrete locations within the physician's discretion or as requested by patients on an individual basis). Such wavelengths are preferably greater than or equal to about 1064 nm, and including without limitation about 1320 nm, about 1470 nm, about 1950 nm, about 2100 nm, about 3000 nm, and about 10,000 nm, each ±about 50 nm.

In some embodiments, the wavelength of the radiation is about 1470 nm, ± about 30 nm, the power is less than about 10 W, preferably less then about 8 W, more preferably less than about 5 W, and most preferably within the range of about 1 W to about 3 W. In one embodiment, the laser is fired in a continuous mode (although a pulsed mode may be employed, if desired), and the laser is pulled back at a rate within the range of about 1 sec/cm to about 20 sec/cm, more preferably within the range of about 3 sec/cm to about 15 sec/cm, and most preferably within the range of about 5 sec/cm to about 10 sec/cm. In one exemplary embodiment, an approximately 10 cm length of a GSV was closed by substantially radially applying approximately 1470 nm radiation, at a power level of about 2 W, at a pullback rate of about 5 sec/cm. In this particular example, a local infiltrate anesthetic was applied only at the access site, and was not applied nor otherwise needed throughout the remainder of the procedure.

In other exemplary embodiments, a plurality of different veins (GSV) were closed by employing a flat-tipped fiber sealed within a quartz cap (see FIG. 10). The radiation was about 1470 nm, and the energy per unit length delivered to the blood vessel was on average about 10 J/cm (i.e., about 1 W at a pullback rate of about 10 sec/cm). In each of these cases, no local tumescent or general anesthetic was employed. Rather, a local infiltrate anesthetic (½% Lidocaine without Epinephrine) was applied only at the patient's request or at the physician's discretion. In some cases, the patients had no anesthetic. In other cases, a small amount was applied at the access site. In other cases, a small amount was applied at the access site and adjacent to the SFJ. One reason for applying a small amount of such local anesthetic in the areas adjacent to the SFJ is because the diameter of the vein typically is largest in this area, and therefore the pullback rate, and thus the average energy per unit length delivered on average to the blood vessel in this region, may be higher than in the distally located treatment areas.

In other exemplary embodiments, a plurality of different varicose veins (GSV) were closed by employing a flat-tipped fiber sealed within a quartz cap (see FIG. 10). The wavelength of radiation applied was about 1470 nm. The primary protocol was to deliver the radiation at a rate within the range of about 20 J/cm to about 30 J/cm; however, some patients received lower energy delivery rates (within the range of about 10 J/cm to about 20 J/cm), and therefore the energy per unit length delivered was on average within the range of about 10 J/cm to about 30 J/cm (the average was about 22 J/cm). The primary protocol also was to deliver radiation at a power level of about 3 W in continuous mode; however, some patients received about 3 W pulsed at a 50% duty cycle (about ½ second on and about ½ second off). The vein diameters were within the range of about 3 mm to about 22 mm (the average vein diameter was about 8.2 mm). All procedures were performed without any tumescent anesthesia or general anesthesia, or any pre-shaping or other compression of the veins. Several patients did not receive any anesthetic at all, and others received a relatively small volume of local infiltrate anesthetic (½% Lidocaine without Epinephrine). Of the 31 patients treated, the average volume of local anesthetic used throughout the entire procedure was about 28 ml, and 7 patients received less than 10 ml. As a general matter, it is believed that the lower the energy delivery rate, the lesser is the volume of anesthetic required or otherwise desired. In addition, as a general matter, pulsed delivery of the laser radiation involved lesser volumes of anesthetic than continuous mode delivery. In all cases, the anesthetic was applied locally as deemed necessary by the physician, or as requested by the patient. The 24 hours post-op results demonstrated that over 90% of the treated veins were occluded with excellent vein wall thickening. In addition, post-op eccymosis and reported pain were almost nil; some bruising was reported in only about 5 to 10% of the patients, primarily at the vein access site; and reported post-op discomfort was minimal with a small number of patients reporting use any of OTC pain relief (e.g., aspirin, acetaminophen, etc.).

Accordingly, a significant advantage of the currently preferred embodiments is that neither local tumescent anesthesia nor general anesthesia are required. As indicated above, in many cases, only a small amount of local infiltrate anesthesia may be applied at the access site to the vein, if at all needed. If during the procedure the patient feels any discomfort, the physician may apply a small amount of local infiltrate anesthetic (e.g., Lidocaine preferably without Epinephrine) at the location or area of discomfort. In any event, no more than about 1 vial (about 50 ml) of local infiltrate anesthesia (e.g., 0.5% Lidocaine without Epinephrine) is required on hand during the procedure, and only a small portion of such vial, if any, may be needed depending on the length of the vein to be treated and/or the sensitivity of the patient to any discomfort perceived or otherwise encountered.

In other embodiments, any of numerous other methods or treatments that are currently known, or that later become known, may be employed to relax the patient and/or to produce analgesia, anesthesia, and/or a decreased sensitivity to painful stimuli. Such methods or treatments include without limitation electroanalgesia, electroanesthesia, neurostimulation, neuromodulation, and other physical or verbal methods of producing analgesia, anesthesia, and/or decreased sensitivity to painful stimuli. Other such methods include analgesia by electrical current based on, for example, transcutaneous or percutaneous nerve stimulation, deep stimulation, posterior spinal cord stimulation, and transcutaneous cranial electrical stimulation. The foregoing description of anesthetics and analgesics is not intended to imply that any anesthetic or analgesic is required in connection with the disclosed endoluminal treatment devices and methods. Rather, many preferred embodiments do not employ any anesthetic or analgesic at all, or at most employ a small amount of local anesthetic or analgesic at an access site or other discrete location to address any localized pain that is perceived or otherwise encountered by the patient.

Accordingly, a significant advantage of the devices and procedures disclosed herein is that the above-described drawbacks associated with the tumescent technique may be avoided, including the potential toxicity and/or adverse patient reactions associated with such anesthetics, the higher incidences of thermal damage to surrounding tissues, and the post operative pain and bruising encountered with the relatively high-energy levels employed with the tumescent technique procedures. Another advantage of the currently preferred embodiments over prior art tumescent technique procedures is that the blood vessel is maintained at approximately the same size prior to and after introduction of the energy application device into the blood vessel, and the energy is applied into the surrounding wall of the blood vessel substantially without pre-shaping, flattening, compressing or moving the wall of the blood vessel toward the energy application device.

As described above, the cap or other structure at the emitting end of the fiber imparts a rounded, relatively large diameter distal region to the fiber tip, thus facilitating ease of insertion into and pullback through a vein. Another advantage of such expanded fiber tip structure in comparison to prior art bare tip fibers is that it displaces a greater volume or portion of the vein lumen. Yet another advantage of some currently preferred embodiments is that the laser radiation is emitted radially and annularly from the fiber into a surrounding annular region of the vein wall, thus transmitting the radiation more directly and efficiently into the vein wall in comparison to prior art ELA methods and devices. Yet another advantage of some currently preferred embodiments is that the optical fiber tip may define a significantly greater emitting surface area in comparison to prior art bare tip or other flat emitting end face fibers, and further, the radiation is emitted laterally/radially. As a result, the laser radiation is transmitted directly into a significantly larger area of surrounding vein wall tissue, and thus may be transmitted at significantly lower power densities in comparison to prior art ELA procedures, to thereby facilitate treatment substantially without localized hot spots that otherwise might cause vein wall perforations, overheating of surrounding tissues, and associated pain and/or discomfort to the patient. Accordingly, a further advantage of the currently preferred embodiments is that they may use significantly lesser power levels in comparison to prior art ELA procedures.

A further advantage of some currently preferred embodiments is that the laser wavelengths employed are highly absorbed in water, and thus highly absorbed in the blood vessel wall tissue. As a result, the laser radiation is directly transmitted into and absorbed by the surrounding annular portion of the vessel wall or otherwise by a sufficient depth of intravascular endothelium to kill or damage the absorbing endothelium and, in turn, achieve blood vessel closure. The terms blood vessel closure, close the blood vessel, occlude the blood vessel, or like terms, are used herein to mean closure or shrinkage of the blood vessel that is sufficient to substantially prevent the flow of blood through the blood vessel following treatment of the blood vessel. Yet another advantage of some currently preferred embodiments is that because the laser radiation is directly and efficiently transmitted into and absorbed by the vessel wall, any significant amount of radiation absorption by the surrounding tissues, and resulting thermal damage, is substantially avoided. As a result, the currently preferred embodiments not only require less power input than do prior art ELA procedures, but require less anesthetic, if any, and allow for the elimination of local tumescent anesthesia and its various drawbacks and disadvantages.

If desired, a saline flush, such as a cold saline flush, may be employed to cool and/or numb the vein prior to lasing and fiber pullback. In some such embodiments, the saline flush is ice cold (e.g., about 30° F. to about 40° F., and more preferably about 32° F. to about 35° F.) to facilitate numbing the vein prior to treatment. In one embodiment, the cold saline flush is introduced into the vein through an introducer sheath and prior to insertion of the fiber. In another embodiment, a cold saline flush is introduced through an introducer sheath after insertion of the fiber and/or during withdrawal of the introducer sheath prior to lasing. In another embodiment, the cold saline flush is introduced through a sheath surrounding the fiber during lasing and pullback of the fiber. In the latter embodiment, the cold saline is introduced through one or more outlet ports located proximate to the emitting tip of the fiber (e.g., at the base of the quartz cap). One such embodiment employs a conventional liquid cooled fiber sheath construction.

In some embodiments ultrasound energy is applied to the fiber or other waveguide to facilitate smooth pullback through the vein and/or pullback at a substantially constant or other desired rate. In one embodiment, an ultrasound transducer or vibrator is connected to the proximal end of the fiber to impart ultrasound vibrations to the emitting tip or region of the fiber during lasing and pullback. In another embodiment, the ultrasound transducer or vibrator is attached to the cap or otherwise adjacent to the emitting tip or region of the fiber to impart ultrasound vibrations thereto during lasing and pullback through the vein.

In another preferred embodiment, the optical fiber set adds three or more shape-memory expandable arms. While inserting the treatment set, the expandable arms are in complete contact with a protective coating. Once in appropriate position, the expandable arms are activated by means of an internal/external energy source, expanding their distal ends, until contacting the inner surface of the blood vessel. As a consequence, the optical fiber set is substantially centered inside the target tissue to further facilitate substantially evenly heating the inner surface and further preventing vein wall contact or perforation. The substantially evenly-heated surface should in turn more uniformly contract, and efficiently shrink the blood vessel to closure where desired.

In the currently preferred embodiments, the wavelengths are selected to offer a reasonably high absorption in the target tissue, such about 1470 nm, ±about 30 nm, and/or about 1950 nm, ±about 30 nm. As may be recognized by those of ordinary skill in the pertinent art, these wavelengths are only exemplary, however, and any of numerous other wavelengths that are currently known, or that later become known, equally may be used, including without limitation about 810 nm, 940 nm, 980 nm, 1064 nm, 1320 nm, 2100 nm, 3000 nm, and 10,000 nm, each ±about 30 nm. One advantage of the 1470 nm and 1950 nm wavelengths is that they are highly absorbed in water, and thus are highly absorbed in the target tissue of the blood vessel wall. Absorption of 1470 nm and 1950 nm in the tissue of a blood vessel wall are about 1-3 orders higher than for 980 nm, and significantly higher than that order for most other commercially available wavelengths.

The protective radiation transparent caps of the currently preferred embodiments may be manufactured and assembled to the fiber in accordance with the teachings of commonly assigned U.S. patent application Ser. No. 11/592, 598, filed 3 Nov. 2006, entitled "Side Fire Optical Fiber For High Power Applications", which is hereby expressly incorporated by reference in its entirety as part of the present disclosure. The fibers and other components of the devices may be the same as or similar to the devices, components or various aspects thereof disclosed in commonly assigned U.S. provisional patent application Ser. No. 61/067,537, filed Feb. 28, 2008 under Express Mail No. EB429577158US, entitled "Rapid Insertion Device And Method For Improved Vascular Laser Treatment", which is hereby expressly incorporated by reference in its entirety as part of the present disclosure.

As indicated above, in certain preferred embodiments, blood vessel wall closure is achieved by thermally damaging or killing on average at least about ⅓ the thickness of the intravascular endothelium, or thermally damaging or killing a depth of intravascular endothelium on average that is within the range of about ⅓ to about ⅔ its thickness. As also indicated above, wavelengths that are strongly absorbed in water and applied at predetermined energy delivery rates are substantially entirely absorbed at a depth of at least about ⅓, or within the range of about ⅓ to about ⅔, the thickness of the intravascular endothelium to, in turn, prevent transmission of any significant level of radiation into surrounding tissues, and thereby avoiding the need for anesthetic along the treated vessel. Intravascular endothelium may be damaged to facilitate blood vessel closure with mechanisms other than radiation. For example, U.S. Pat. No. 6,402,745 ("the '745 patent") shows an intravenous whip electrode for vein ablation, and is hereby incorporated by reference in its entirety as part of the present disclosure. Some embodiments of the '745 patent do not deliver electrical energy to the intravascular endothelium, whereas other embodiments do. In accordance with one embodiment of the present disclosure, the intravenous device includes a rotating whip or other device for scraping or abrading the intravascular endothelium as disclosed, for example, in the '745 patent, and an integral intravascular energy application device that delivers sufficient energy to the intravascular endothelium that, combined with the scraping or abrading action of the whip or other device, sufficiently damages at least about ⅓ to about ⅔ the depth of the endothelium to achieve blood vessel closure. In some such embodiments, the energy application device is an optical waveguide that delivers radiation wavelengths strongly absorbed in water (i.e., about 1064 nm or greater). In some such embodiments, the radiation is pulsed to allow relatively high energy delivery rates substantially without any anesthetic along the treated segment(s) of the blood vessel. The abrading or scraping action of the whip or like device may allow for even lower energy delivery rates to the blood vessel wall to sufficiently damage the vessel to closure without the use of an anesthetic along the treated segment(s) of the vessel.

Having described various preferred embodiments with reference to the accompanying drawings, it is to be understood that the invention is not limited to these precise embodiments, and that various changes and modifications may be effected therein by those skilled in the art without departing from the scope or spirit of the invention as defined in the appended claims. For example, the radiation can be emitted in a pulsed or continuous mode and can contain one or more laser wavelengths. In addition, the radiation can be supplied by means other than lasers, including without limitation, by LEDs and super luminescent LEDs. In addition, the optical fibers may take the form of any of numerous different optical fibers or waveguides that are currently known or that later become known, that may define any of numerous different cores, claddings, jackets, end caps, protective sleeves, emitting surfaces, reflective surfaces, and/or gradient lenses, that are currently known, or that later become known. For example, although many of the fibers disclosed herein are capped, fibers without caps, including bare tipped fibers, may be employed. Further, the emitting surfaces may take any of numerous different shapes or configurations that are currently known, or that later become known. For example, although certain embodiments employ emitting surfaces that are substantially conical shaped, emitting surfaces defining other arcuate surface contours (i.e., surface contours that are curved), or defining non-arcuate surface contours, such as one or more flat, and/or angled emitting surfaces, equally may be employed. In addition, the methods of venous treatment may employ any of numerous different devices with or without anesthetics, including without limitation, without sheaths or catheters, or with any of numerous different types of sheaths or catheters, including without limitation short, long and/or tear away introducer sheaths, without guide wires, or with guide wires, including without limitation, guide wires attached to, detachable from, or not at all attached to the fiber or waveguide. In addition, any of numerous different forms of energy and energy application devices that are currently known, or that later become known, equally may be employed to treat blood vessels in accordance with various aspects of the inventions disclosed herein. For example, the energy application device may take the form of (i) a waveguide or optical fiber that emits laser energy as described above; (ii) a microwave catheter or device that emits microwave energy; (iii) an RF catheter or device that emits RF energy; (iv) an electrical catheter or device that emits electrical energy; and (v) an ultrasound catheter or device that emits ultrasound energy. Accordingly, this detailed description of currently preferred embodiments is to be taken in an illustrative as opposed to a limiting sense.

What is claimed is:

1. A device for endoluminal treatment of a blood vessel having a vessel wall, comprising:
a flexible waveguide comprising an optical fiber and a cladding, said flexible waveguide defining an elongated axis, the flexible waveguide comprising a proximal end optically connectable to a source of radiation and a distal end receivable within the blood vessel, the flexible waveguide including, at the distal end, an optical fiber tip having a conical shape and defining a convex radiation emitting surface that is acutely angled with respect to the elongated axis of the waveguide;
a reflective cone axially spaced relative to the radiation emitting surface and facing the radiation emitting surface such that the apex of the radiation emitting surface and the apex of the reflective cone are coaxial and face each other;
and a cylindrical tubular cover that is fixedly secured to the distal end of the waveguide and sealed with respect thereto, the cover enclosing the radiation emitting surface and the reflective cone and defining an air gap between the radiation emitting surface and the reflective cone;
wherein the angled radiation emitting surface and the reflective cone are configured to laterally emit 360° radial radiation and produce an annular beam of radiation onto a circumferential portion of the surrounding vessel wall, the center of said beam being emitted at an angle of between 70° and 90° relative to the waveguide axis.

2. The device as defined in claim 1, further comprising a cylindrical tubular cover, wherein the cover is a cap that is transparent with respect to the emitted radiation.

3. The device as defined in claim 1, further comprising a lateral radiation emitting distal region defined by a plurality of regularly spaced radiation emitting grooves in the cladding contained within a cylindrical tubular cover and axially spaced relative to each other along a distal region of the waveguide, whereby radiation is emitted from said optical fiber through said grooves.

4. The device as defined in claim 3, wherein each radiation emitting groove defines an arcuate surface contour angled with respect to the elongated axis of the waveguide that emits a portion of the radiation transmitted through the waveguide laterally with respect to the elongated axis onto a surrounding arcuate portion of the vessel wall and allows the remaining transmitted radiation to pass through the waveguide for lateral emission by any downstream radiation emitting grooves and the radiation emitting surface at the distal end of the waveguide.

5. The device as defined in claim 3, wherein said cylindrical tubular cover encloses the lateral radiation emitting distal region, forms a gas interface at each of the plurality of radiation emitting grooves that is sealed with respect to the exterior of the waveguide, and cooperates with the angled arcuate surface contour of at least a plurality of the radiation emitting grooves to deflect radiation laterally with respect to the elongated axis of the waveguide.

6. The device as defined in claim 5, wherein the cover is transparent with respect to the emitted radiation and is sufficiently flexible to allow the waveguide to bend upon passage through a tortuous blood vessel.

7. The device as defined in claim 3, further comprising a sleeve slidably mounted over the waveguide and defining an internal radiation reflective surface for reflecting laterally emitted radiation inwardly and controlling the axial length of the lateral radiation emitting distal region.

8. The device as defined in claim 1, further comprising a radiation source, a temperature sensor thermally coupled to a distal region of the waveguide for monitoring a temperature within the blood vessel and transmitting signals indicative thereof, and a control module electrically coupled to the temperature sensor for regulating the power output of the radiation source based thereon.

9. The device as defined in claim 8, further comprising a pullback actuator drivingly coupled to the waveguide for controlling the pullback speed of the waveguide, and wherein the control module is electrically coupled to the pullback actuator for regulating the pullback speed of the waveguide based on the temperature at the distal region of the waveguide.

10. The device of claim 1, further comprising a guide wire engagement member mechanically coupled to the cover to detachably engage a guide wire therewith, wherein the guide wire engagement member is configured to engage the guide wire while being advanced in the blood vessel and configured to disengage the guide wire while being extracted from the blood vessel.

11. The device as defined in claim 1, further comprising a guide wire fixedly secured to the tip of the waveguide and extending distally therefrom.

12. The device as defined in claim 11, wherein the guide wire is fixedly secured to the cover and extends distally therefrom.

13. The device as defined in claim 1 for endoluminal laser ablation, further comprising at least one laser source that provides laser radiation of at least one of 1470 nm and 1950 nm, each ±30 nm, at a power of less than or equal to 10 W, wherein the proximal end of the waveguide is optically coupled to the at least one laser source, and wherein the emitting surface of the waveguide emits radiation laterally with respect to the elongated axis of the waveguide in an axially-extending, annular pattern onto the surrounding vessel wall.

14. The device as defined in claim 13, further comprising an electric pullback device drivingly coupled to the waveguide and configured to pullback the waveguide through the blood vessel while delivering laser radiation at an energy delivery rate of less than 30 J/cm on average to the blood vessel wall.

15. A device for endoluminal treatment of a blood vessel, comprising:
a flexible waveguide comprising an optical fiber and a cladding, said flexible waveguide defining an elongated axis, the flexible waveguide comprising a proximal end optically connectable to a source of radiation and a distal end receivable within the blood vessel, wherein the distal end of the flexible waveguide includes:
first means for emitting radiation laterally with respect to the elongated axis of the waveguide and producing an annular beam of radiation onto an angularly extending portion of the surrounding vessel wall, and
second means for emitting radiation laterally with respect to the elongated axis of the waveguide and annularly from the waveguide along an axially-extending region of the waveguide,
wherein the first means for emitting radiation laterally includes an optical fiber tip having a conical shape and defining a radiation emitting surface that is acutely angled with respect to the elongated axis of the waveguide and a reflective cone axially spaced with respect to the radiation emitting surface and facing the radiation emitting surface such that the apex of the radiation emitting surface and the apex of the reflective cone are coaxial and face each other, and
wherein the second means for emitting radiation includes a plurality of radiation emitting grooves in said cladding proximally located with respect to said first means for emitting radiation and axially regularly spaced relative to each other, whereby radiation is emitted from said optical fiber through said grooves; and
a cylindrical tubular cover coupled to the distal end of the waveguide and enclosing said first and second means for emitting radiation laterally therein, the cover defining an air gap between the radiation emitting surface and the reflective cone and at each of the plurality of radiation emitting grooves.

16. The device as defined in claim 15, further comprising means for adjusting the length of the second means for emitting radiation.

17. The device as defined in claim 16, wherein the means for adjusting includes a sleeve slidably mounted on the waveguide.

18. The device as defined in claim 15, further comprising means for pulling back the waveguide through the blood vessel while delivering laser radiation at an energy delivery rate of less than 30 J/cm on average to the blood vessel wall.

19. A method for endoluminal treatment of a blood vessel, comprising the following steps:
(i) introducing a device according to claim 1 into the blood vessel;
(ii) transmitting radiation through the waveguide; and
(iii) emitting radiation laterally with respect to the elongated axis of the waveguide onto an angularly extending portion of the surrounding vessel wall.

20. The method as defined in claim 19, wherein the emitting step includes laterally emitting radiation onto a circumferential portion of the surrounding vessel wall by an annular beam of radiation whose center extends throughout an angle of between 70° and 90° relative to the waveguide axis.

21. The method as defined in claim 20, wherein the emitting step includes laterally emitting radiation onto a circumferential portion of the surrounding vessel wall extending throughout an angle of 360°.

22. The method as defined in claim 21, further comprising laterally emitting radiation at a power of less than 10 W.

23. The method as defined in claim 22, further comprising laterally emitting radiation at a power of less than 5 W.

24. The method as defined in claim 21, further comprising the step of reflecting forwardly emitted radiation laterally with respect to the elongated axis in an annular pattern onto the surrounding vessel wall.

25. The method as defined in claim 21, further comprising the step of transmitting the radiation at a power of less than 10 W at a wavelength within the range of 980 nm to 1900 nm.

26. The method as defined in claim 25, wherein the wavelength is within the range of at least one of (i) 950 nm to 1110 nm, (ii) 1440 nm to 1500 nm, and (iii) 1870 nm to 1930 nm.

27. The method as defined in claim 21, further comprising the step of withdrawing the waveguide through the blood vessel during step (iii).

28. The method as defined in claim 21, further comprising the step of applying a local infiltrate anesthetic at an access site prior to introducing the waveguide through the access site and into the blood vessel.

29. The method as defined in claim 28, further comprising the step of applying a local infiltrate anesthetic during step (iii), or interrupting step (iii) and applying a local infiltrate anesthetic, to a localized region of tissue to relieve any pain or discomfort at the localized region.

30. The method as defined in claim 27, further comprising performing the entire endoluminal treatment procedure without the use of local tumescent anesthesia or general anesthesia.

31. The method as defined in claim 30, further comprising the step of emitting radiation that is within the range of at least one of (i) 1440 nm to 1500 nm and (ii) 1870 nm to 1930 nm, at a power of less than 10 W; applying the emitted radiation radially with respect to the elongated axis of the waveguide throughout 360° in an annular pattern onto a circumferential portion the surrounding vessel wall; and withdrawing the waveguide through the blood vessel during the applying step.

32. The method as defined in claim 31, further comprising the step of emitting radiation at a power within the range of 1 W to 3 W and withdrawing the waveguide through the blood vessel at a rate sufficient to thermally damage and close the blood vessel.

33. The method as defined in claim 19, wherein the emitting step includes emitting diffuse radiation along an axially-extending region of the waveguide laterally into the surrounding vessel wall.

34. The method as defined in claim 33, wherein the emitting step includes emitting the radiation radially with respect to the elongated axis of the waveguide throughout 360° in an annular pattern onto a circumferential portion the surrounding vessel wall.

35. The method as defined in claim 19, further comprising the step of introducing a cold saline solution into the vessel lumen prior to or during the emitting step.

36. The method as defined in claim 19, further comprising the step of vibrating at least one of the waveguide and the distal tip thereof to facilitate at least one of (i) a smooth flowing pullback of the waveguide through the blood vessel and (ii) pullback through the blood vessel at a constant rate.

37. The device as defined in claim 10, wherein a distal portion of the guide wire extends distally beyond the distal tip of the waveguide for guiding the waveguide through the blood vessel.

38. The device of claim 15, further comprising a guide wire engagement member coupled with the flexible waveguide to detachably engage a guide wire, wherein the guide wire engagement member is configured to engage the guide wire while being advanced in the blood vessel and configured to disengage the guide wire while being extracted from the blood vessel.

* * * * *